(12) United States Patent
Guenther et al.

(10) Patent No.: US 9,173,886 B2
(45) Date of Patent: Nov. 3, 2015

(54) ANTIVIRAL COMPOUNDS AND METHODS OF USE THEREOF

(75) Inventors: Richard H. Guenther, Cary, NC (US); Jerzy R. Szewczyk, Chapel Hill, NC (US)

(73) Assignee: Trana Discovery, Inc., Cary, NC (US)

( * ) Notice: Subject to any disclaimer, the term of this patent is extended or adjusted under 35 U.S.C. 154(b) by 351 days.

(21) Appl. No.: 13/634,464

(22) PCT Filed: Mar. 14, 2011

(86) PCT No.: PCT/US2011/028397
§ 371 (c)(1),
(2), (4) Date: Nov. 16, 2012

(87) PCT Pub. No.: WO2011/113060
PCT Pub. Date: Sep. 15, 2011

(65) Prior Publication Data
US 2013/0071353 A1 Mar. 21, 2013

Related U.S. Application Data

(60) Provisional application No. 61/313,527, filed on Mar. 12, 2010.

(51) Int. Cl.
*A61K 48/00* (2006.01)
*A61K 31/5375* (2006.01)
(Continued)

(52) U.S. Cl.
CPC ........... *A61K 31/5375* (2013.01); *A61K 31/136* (2013.01); *A61K 31/137* (2013.01); *A61K 31/167* (2013.01); *A61K 31/357* (2013.01); *A61K 31/36* (2013.01); *A61K 31/38* (2013.01); *A61K 31/40* (2013.01); *A61K 31/426* (2013.01); *A61K 31/428* (2013.01); *A61K 31/4245* (2013.01); *A61K 31/437* (2013.01); *A61K 31/4439* (2013.01); *A61K 31/451* (2013.01); *A61K 31/473* (2013.01);
(Continued)

(58) Field of Classification Search
CPC ............ A61K 31/36; A61K 39/39566; A61K 31/428; A61K 31/437; A61K 31/426; A61K 31/4439; A61K 31/451; A61K 31/473
See application file for complete search history.

(56) References Cited

PUBLICATIONS

CID 767399 (http://pubchem.ncbi.nlm.nih.gov/summary/summary.cgi?cid=767399; accessed Sep. 17, 2014).*

(Continued)

*Primary Examiner* — Savitha Rao
*Assistant Examiner* — Angela Brown-Pettigrew
(74) *Attorney, Agent, or Firm* — Andrews Kurth LLP; David Bradin

(57) ABSTRACT

The present invention is drawn to a pharmaceutical composition comprising the following compound:

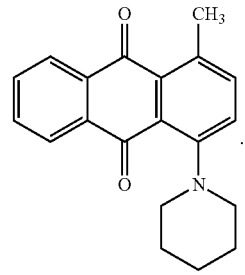

The compound and other azacycle derivatives can be used in method of treatments for retroviral infections, such as HIV.

11 Claims, 4 Drawing Sheets

(51) Int. Cl.
- *A61K 31/36* (2006.01)
- *A61K 31/38* (2006.01)
- *A61K 31/428* (2006.01)
- *A61K 31/437* (2006.01)
- *A61K 31/517* (2006.01)
- *A61K 31/136* (2006.01)
- *A61K 31/137* (2006.01)
- *A61K 31/167* (2006.01)
- *A61K 31/357* (2006.01)
- *A61K 31/40* (2006.01)
- *A61K 31/4245* (2006.01)
- *A61K 31/426* (2006.01)
- *A61K 31/4439* (2006.01)
- *A61K 31/451* (2006.01)
- *A61K 31/473* (2006.01)
- *A61K 31/4743* (2006.01)
- *A61K 31/515* (2006.01)
- *A61K 31/7088* (2006.01)
- *A61K 38/21* (2006.01)
- *A61K 39/395* (2006.01)

(52) U.S. Cl.
CPC .......... *A61K 31/4743* (2013.01); *A61K 31/515* (2013.01); *A61K 31/517* (2013.01); *A61K 31/7088* (2013.01); *A61K 38/21* (2013.01); *A61K 39/39566* (2013.01)

(56) References Cited

PUBLICATIONS

Dokunikhin et al ( Zhurnal Prikladnoi Khimii (Sankt-Peterburg, Russian Federation) (1965), 38(11), 2619-21.*
Ito et al. In Cancer Science 94(1), 3-8 (2003).*
Dokunikhin et al. English Translation. 2015.*

* cited by examiner

ANTIVIRAL COMPOUNDS AND METHODS OF USE THEREOF

CROSS-REFERENCE TO RELATED APPLICATIONS

This application is a U.S. national phase application under the provisions of 35 U.S.C. §371 of International Patent Application No. PCT/US11/28397 filed Mar. 14, 2011, which in turn claims priority of U.S. Patent Application No. 61/313,527 filed Mar. 12, 2010. The disclosures of such international patent application and US priority patent application are hereby incorporated herein by reference in their respective entireties, for all purposes.

FIELD

The invention generally relates to antiviral compounds, compositions including the compounds, and methods of treatment using the compounds.

BACKGROUND

The primate lentiviruses include the human immunodeficiency viruses types 1 and 2 (HIV-I and HIV-2) and simian immunodeficiency viruses (SIVs) (Barre-Sinoussi, F., et al. (1983) Science 220:868-871; Clavel, F. (1987) AIDS 1:135-140; Daniel, M. D., et al. (1985) Science 228:1201-1204; Desrosiers, R. C. (1990) Ann. Rev. Immunol. 8: 557-578; Gallo, R. C, et al. (1984) Science 224:500-503). HIV-1 and HIV-2 infect humans, HIV-1-like viruses infect chimpanzees, and SIV variants infect African monkeys. Humans infected by HIV-1 and HIV-2 and Asian macaques infected by certain SIV strains often develop life-threatening immunodeficiency due to depletion of CD4-positive T lymphocytes (Fauci, A., et al. (1984) Ann. Int. Med. 100:91-106; Letvin, N. L., et al. (1985) Science 230:71-739, 19).

In humans, HIV infection causes Acquired Immunodeficiency Syndrome (AIDS), an incurable disease in which the body's immune system breaks down leaving the victim vulnerable to opportunistic infections, e.g., pneumonia and certain cancers, e.g., Kaposi's Sarcoma. AIDS is a major global health problem. The Joint United Nations Programme on HIV/AIDS (UNAIDS) estimates that there are now over 34 million people living with HIV or AIDS worldwide; some 28.1 million of those infected individuals reside in impoverished subSaharan Africa. In the United States, approximately one out of every 500 people are infected with HIV or have AIDS. Since the beginning of the epidemic, AIDS has killed nearly 19 million people worldwide, including some 425,000 Americans. AIDS has replaced malaria and tuberculosis as the world's deadliest infectious disease among adults and is the fourth leading cause of death worldwide.

There remains a need for the identification of inhibitors of retroviral infection.

SUMMARY

Compounds which are inhibitors of retroviral propagation are disclosed. Methods of treating and/or preventing retroviral infection using the inhibitors of retroviral propagation, and pharmaceutical compositions including the inhibitors and a pharmaceutically-acceptable carrier, are also disclosed. Combination therapy using one or more of the inhibitors, and a second anti-retroviral compound, are also disclosed.

The compounds inhibit retroviral propagation by inhibiting retroviral reverse transcription, viral recruitment of the retroviral primer used in translation, human tRNA$^{Lys3}$, inhibiting the final packaging and assembly of new virions, and/or inhibiting the binding of a host cell tRNA to a target nucleic acid molecule.

The inhibitory activity of the compounds can be evaluated using methods for screening inhibitors of retroviral propagation. Such methods may involve forming a mixture comprising a linear sequence of a tRNA anticodon stem loop fragment, a nucleic acid molecule capable of binding to the tRNA anticodon stem loop fragment, and a test compound. The mixture is incubated under conditions that allow binding of the tRNA anticodon stem loop fragment and the nucleic acid molecule in the absence of the test compound. One can then determine whether or not a test compound inhibits the propagation of a retrovirus. Inhibition of binding of the tRNA ASL fragment and the target nucleic acid molecule is indicative of the test compound being an inhibitor of retroviral propagation.

DETAILED DESCRIPTION

Figure 1:
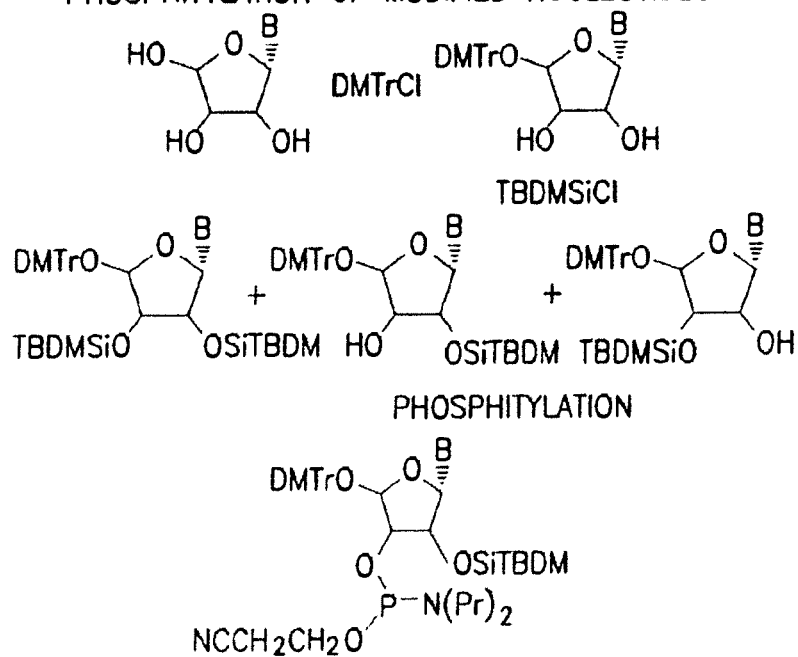
FIG. 1 provides a schematic representation of the protection of the modified nucleotides prior to synthesis of the RNA oligomer. Panel A illustrates protection with trifluoryl acetic acid. Panel B illustrates protection with benzoyl. Panel C illustrates the general protection of the ribose hydroxyl groups.
Figure 2:
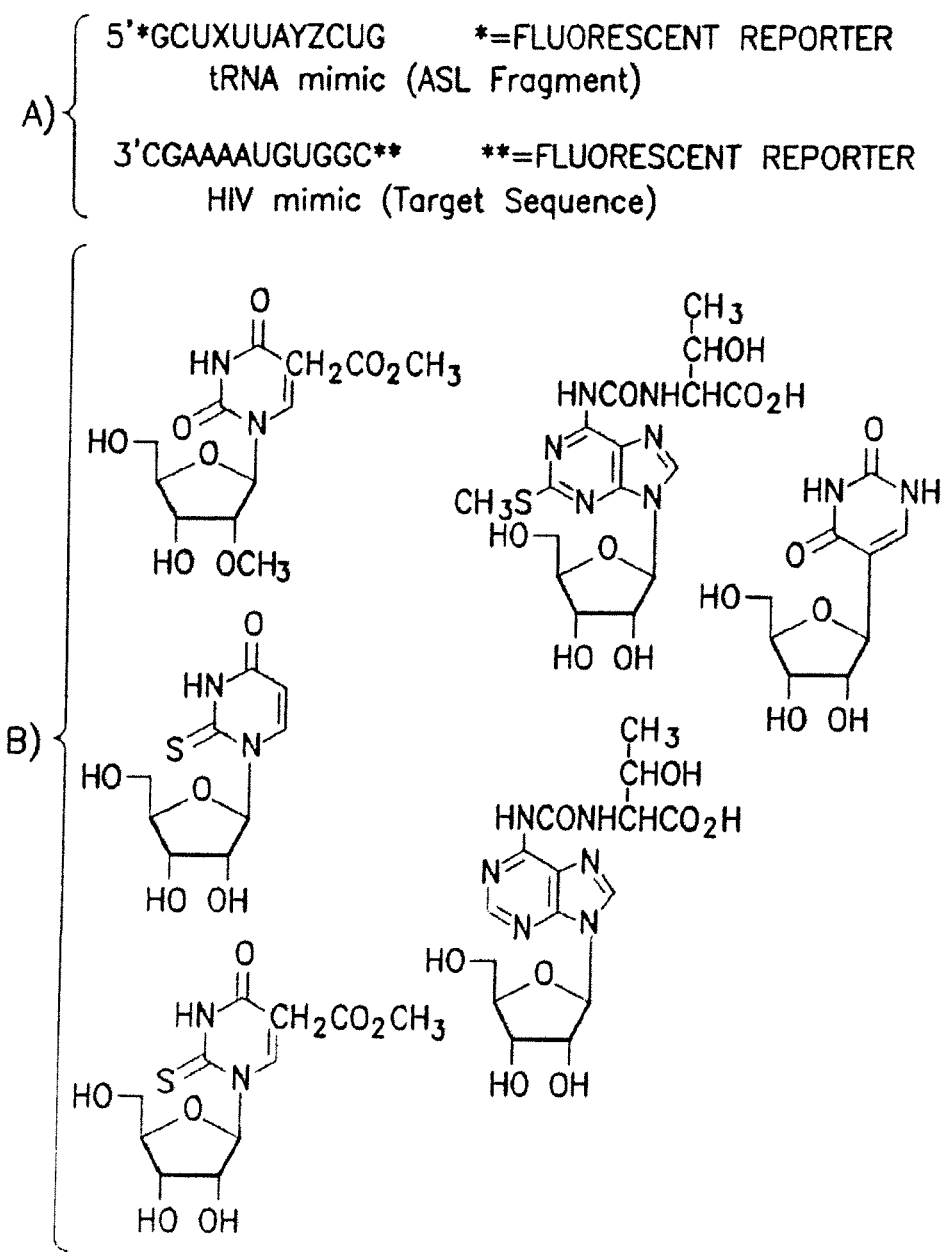
FIG. 2A provides a representation of a labeled tRNA fragment and a corresponding target sequence.
FIG. 2B provides structures of several representative modified nucleosides.

The present invention relates to compounds which inhibit retroviral propogation, compositions including the compounds, and methods of treating and/or preventing retroviral infection using the compounds. Viral propagation can be inhibited by inhibiting reverse transcription, viral replication, translation of viral RNA into proteins, recruitment of human tRNA$^{Lys3}$, packaging and assembly of new virions, and/or inhibiting the binding of a host cell tRNA to a target nucleic acid molecule.

Prior to describing this invention in further detail, however, the following terms will first be defined.

DEFINITIONS

As used herein, an "inhibitor" refers to any compound capable of preventing, reducing, or restricting retroviral propagation. An inhibitor may inhibit retroviral propagation, for example, by preventing, reducing or restricting retroviral reverse transcription. In some embodiments, the inhibition is at least 20% (e.g., at least 50%, 70%, 80%, 90%, 95%, 98%, 99%, 99.5%) of the retroviral propagation as compared to the propagation in the absence of the inhibitor. In one aspect, an inhibitor prevents, reduces, or restricts the binding of a tRNA, or fragment thereof, to a target nucleic acid molecule. Inhibitors can also affect recruitment of human tRNA$^{Lys3}$, translation of viral RNA into proteins, and/or final packaging and assembly of virions. Assays for analyzing inhibition are described herein and are known in the art.

An "RNA-dependent DNA polymerase" or "reverse transcriptase" is an enzyme that can synthesize a complementary DNA copy ("cDNA") from an RNA template. All known reverse transcriptases also have the ability to make a complementary DNA copy from a DNA template (target nucleic acid); thus, they are both RNA- and DNA-dependent DNA polymerases.

As used herein, a "label" or "detectable label" is any composition that is detectable, either directly or indirectly, for example, by spectroscopic, photochemical, biochemical, immunochemical, or chemical means. Useful labels include, but are not limited to, radioactive isotopes (for example, 32p, 35S, and 3H), dyes, fluorescent dyes (for example, Cy5 and Cy3), fluorophores (for example, fluorescein), electron-dense reagents, enzymes and their substrates (for example, as commonly used in enzyme-linked immunoassays, such as, alkaline phosphatase and horse radish peroxidase), biotin-streptavidin, digoxigenin, or hapten; and proteins for which antisera or monoclonal antibodies are available. Moreover, a label or detectable moiety can include an "affinity tag" that, when coupled with the target nucleic acid and incubated with a test compound or compound library, allows for the affinity capture of the target nucleic acid along with molecules bound to the target nucleic acid. One skilled in the art will appreciate that an affinity tag bound to the target nucleic acid has, by definition, a complimentary ligand coupled to a solid support that allows for its capture. For example, useful affinity tags and complimentary partners include, but are not limited to, biotin-streptavidin, complimentary nucleic acid fragments (for example, oligo dT-oligo dA, oligo T-oligo A, oligo dG-oligo dC, oligo G-oligo C), aptamers, or haptens and proteins for which antisera or monoclonal antibodies are available. The label or detectable moiety is typically bound, either covalently, through a linker or chemical bound, or through ionic, van der Waals or hydrogen bonds to the molecule to be detected.

The terms "alkyl", "aryl" and other groups refer generally to both unsubstituted and substituted groups unless specified to the contrary.

Unless specified otherwise, alkyl groups are hydrocarbon groups and are preferably $C_1$-$C_{15}$ (that is, having 1 to 15 carbon atoms) alkyl groups, which can be branched or unbranched, acyclic or cyclic. The above definition of an alkyl group and other definitions would apply also when the group is a substituent on another group (for example, an alkyl group as a substituent of an alkylamino group or a dialkylamino group).

The term "aryl" refers to any functional group or substituent derived from a simple aromatic ring, such as phenyl, thiophenyl, indoyl, etc.

The term "alkenyl" refers to a straight or branched chain hydrocarbon group with at least one double bond, preferably with 2-15 carbon atoms.

The term "alkynyl" refers to a straight or branched chain hydrocarbon group with at least one triple bond, preferably with 2-15 carbon atoms.

The terms "alkylene," "alkenylene" and "alkynyllene" refer to bivalent forms of alkyl, alkenyl, and alkynyl groups, respectively.

The terms "halogen" or "halo" refer to fluoro, chloro, bromo, or iodo.

Substituent groups building off of the hydrocarbon groups include alkoxy, aryloxy, acyloxy, haloalkyl, perfluoroalkyl, fluorine, chlorine, bromine, carbamoyloxy, hydroxyl, nitro, cyano, cyanoalkyl, azido, azidoalkyl, formyl, hydrazine, hydroxyalkyl, alkoxyalkyl, and the like.

I. Antiviral Compounds

The compounds generally have one of the following formulas:

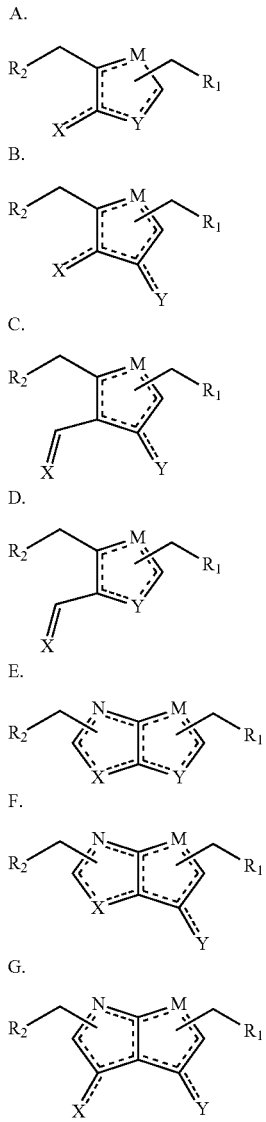

wherein:

══ Single or double bond, with the proviso that no allenes are intended to be within the scope of the invention.

M and N=1, 2 or 3 atoms from C, N, O

X and Y=$NR^1$, O or S $R^1$=H, alkyl, aryl, aralkyl, alkaryl, heterocyclyl, heteroaryl, substituted analogs thereof, wherein the substituents are selected from the list of substituents, Z, defined herein.

Substituents Z as defined herein include $C_{1-6}$ alkyl (including cycloalkyl), alkenyl, heterocyclyl, aryl, heteroaryl, halo (e.g., F, Cl, Br, or I), —OR', —NR'R", —$CF_3$, —CN, —$NO_2$, —$C_2R'$, —SR', —$N_3$, —C(═O)NR'R", —NR'C(═O) R", —C(═O)R', —C(═O)OR', —OC(═O)R', —OC(═O) NR'R", —NR'C(═O)O R", —$SO_2$R', —$SO_2$NR'R", and —NR'$SO_2$R", where R' and R" are individually hydrogen, $C_{1-6}$ alkyl, cycloalkyl, heterocyclyl, aryl, or arylalkyl (such as benzyl).

More specifically, within these broad formulas are the following representative narrower formulas:

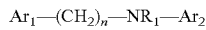

Ar$_1$—(CH$_2$)$_n$—NR$_1$—Ar$_2$　　　　Formula A wherein Ar$_1$ and Ar$_2$ are, independently, six membered aryl rings, five or six membered ring heteroaryl rings, or analogs thereof in which a five membered heteroaryl or six membered aryl or heteroaryl ring is fused to the six membered aryl rings, five or six membered ring heteroaryl rings, n is 0 or 1, and R$_1$ is H or a moiety cleaved in vivo to form H, and each of the aryl/heteroaryl rings can be substituted with one to three substituents, Z.

Substituents Z as defined herein include C$_{1-6}$ alkyl (including cycloalkyl), alkenyl, heterocyclyl, aryl, heteroaryl, halo (e.g., F, Cl, Br, or I), —OR', —NR'R", —CF$_3$, —CN, —NO$_2$, —C$_2$R', —SR', —N$_3$, —C(=O)NR'R", —NR'C(=O) R", —C(=O)R', —C(=O)OR', —OC(=O)R', —OC(=O)NR'R", —NR'C(=O)O R", —SO$_2$R', —SO$_2$NR'R", and —NR'SO$_2$R", where R' and R" are individually hydrogen, C$_{1-6}$ alkyl, cycloalkyl, heterocyclyl, aryl, or arylalkyl (such as benzyl).

In one embodiment, where one or more aryl rings are present, at least one of the rings is an aniline or substituted aniline (i.e., an aryl ring with an —NH$_2$, primary amine, or secondary amine substituent).

Representative compounds from the table provided above, in which n is 0, Ar$_1$ is phenyl, and Ar$_2$ is pyridinyl or pyrimidinyl, include Compounds 66, 73, and 111.

Compounds 16, 20, and 27 are compounds in which n is 0, Ar$_1$ and Ar$_2$ are pyrimidinyl, and one of the pyrimidinyl rings is fused to an aryl ring.

Compound 62 is a compound in which n is 0, Ar$_1$ is phenyl, and Ar$_2$ is pyridinyl, and the pyridinyl ring is fused to an aryl ring.

Compounds 6, 11, 12, and 90 are compounds in which n is 0, Ar$_1$ is phenyl, and Ar$_2$ is oxathiazole.

Compound 29, 39, and 61 are compounds in which n is 0, and Ar$_1$ and Ar$_2$ are phenyl.

Compounds 25, 33, 37, 42, 51, 52, 53, 69, 79, 80, 87, 99, 100, 107, 112 are compounds in which n is 1, and Ar$_1$ and Ar$_2$ are phenyl.

Compound 58 is a compound in which n is 1, and Ar$_1$ and Ar$_2$ are both phenyl-fused heteroaryl rings.

Compounds 81 and 91 are compounds in which n is 1, Ar$_1$ is phenyl, and Ar$_2$ is a phenyl-fused heteroaryl rings.

Compounds 4, 5, 13, and 15 have a core structure where n is 0, Ar$_1$ is 1H-pyridin-4-one, and Ar$_2$ is a pyrimidine ring fused to a benzene ring, as shown below:

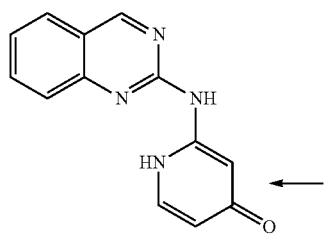 [SMILES: O=c1cc[nH]c(Nc2ncc3ccccc3n2)c1]

Additional representative compounds include the following:

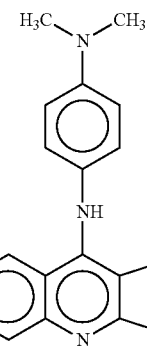

Compound 170

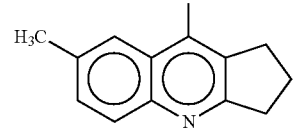

Compound 181

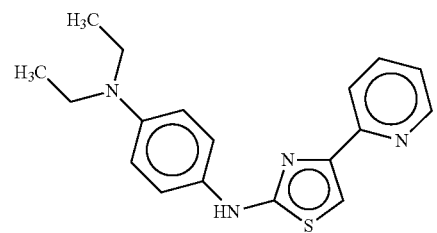

Compound 191

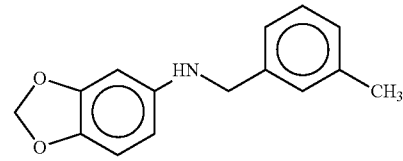

Compound 193

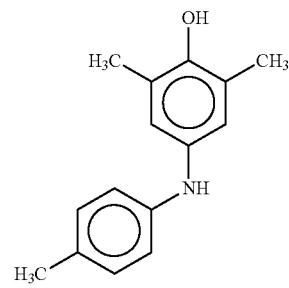

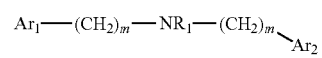

Ar$_1$—(CH$_2$)$_m$—NR$_1$—(CH$_2$)$_m$—Ar$_2$　　Formula B where Ar$_1$, Ar$_2$, and R$_1$ are as defined above, m is 0, 1, 2 or 3, and the aryl/heteroaryl rings can be substituted with from 1 to 3 substituents, Z, as described above, with the proviso that at least one m is 2.

Specific embodiments are those in which one of m is 1 and the other m is 2, both of m are 2, one of m is 0 and the other m is 2, and one of m is 1 and the other m is 3. Compound 21 is an example of a compound where one of m is 0 and the other m is 2. Compounds 19 and 36 are examples of compounds where one m is 1 and the other m is 2. Compounds 50 and 98 are examples of compounds where one m is 1 and the other m is 3. Compounds 50 and 98 both also include a benzofuran ring, and a phenyl ring substituted with a dimethylamine group at a position para to the linkage to the remainder of the molecule.

The following compounds either fall within Formula B, or are closely related to Formula B:

Compound 9

Compound 13

Compound 46

The following compounds fall within Formula B-3 below:

Ar-Q  B-3 wherein Q is selected from the group consisting of —NH—C(NR$_1$)—NH$_2$, —O—C(NR$_1$)—NH$_2$, —S—C(NR$_1$)—NH$_2$, —NH—C(O)—NH$_2$, —O—C(O)—NH$_2$, —S—C(O)—NH$_2$, —NH—C(S)—NH$_2$, O—C(S)—NH$_2$, and —S—C(S)—NH$_2$. Representative compounds falling within the scope of formula B-3 include the following:

where Z, j, and R$_1$ are as defined above.

Compound 122

Compound 188

Compound 349

The modifications of Formula B include the change from an amine linkage to an imine linkage or a C(O)CH$_2$CH$_2$NHC(O) linkage, or the replacement of the —(CH$_2$)$_m$—Ar$_2$ moiety with —C(NH)NH$_2$, where Ar is quinolone or isoquinoline These modifications can be applied across the range of Formula B.

Formula C wherein m is 0, 1, or 2, X is NR$_1$, O, or S, and halo is F, Cl, Br, I. In one embodiment of Formula B, X is S and halo is Cl. Representative azacyclic rings include morpholine, azacyclopentane, and piperidine.

Compounds 31, 44, and 88 are examples of compounds of Formula C.

Formula D where Z, j and $R_1$ are as defined above, with the proviso that two $R_1$ groups can link together to form a 5-7 membered ring azacyclic moiety.

Compounds 9 and 28 are examples of compounds of Formula D.

A structural analog of Formula D is shown below:

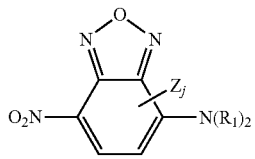

Formula D-A wherein $R_1$, Z and j are as defined above.

Representative compounds of Formula D-A are shown below:

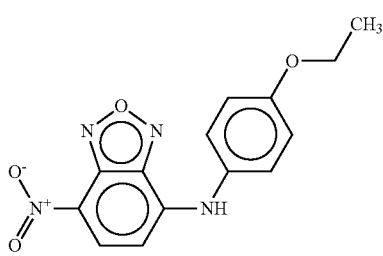

Compound 146

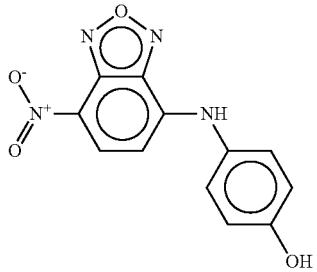

Compound 157

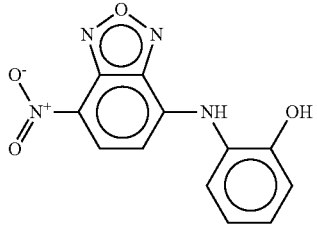

Compound 210

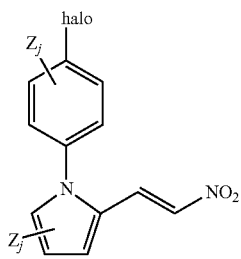

Formula E where Z and j are as defined above.

Compounds 45 and 49 are examples of compounds of Formula E.

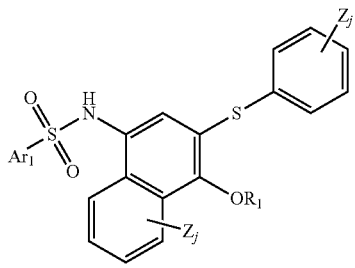

Formula F wherein $Ar_1$, $R_1$, Z and j are as defined above, and $Ar_1$ can include from one to three Z substituents.

Compounds 48, 56, 64, and 77 are representative compounds of Formula F.

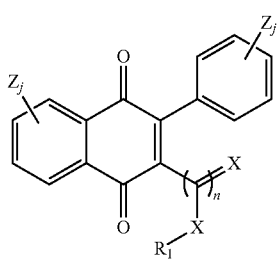

Formula G wherein X, $R_1$, Z, j, and n are as defined above, and the =X moiety can be present or not present (i.e., n is 0 or 1).

Compounds 17, 60, 74, and 96 are representative compounds within the scope of Formula G.

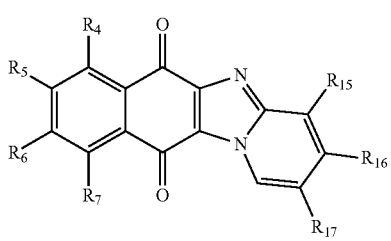

Formula H

Alternatively, the compounds of Formula H can have the formula shown below, where the cyclohexadienone double bond is optional (as indicated by a dashed line), as follows:

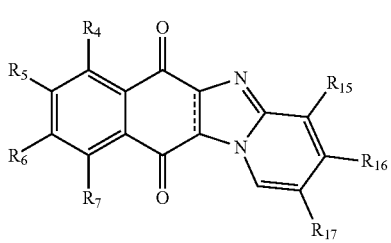

wherein the dashed line indicates the presence of an optional double bond.

The analogs can have substantially any organic substituent or functional group substituted in place of one or more of the hydrogen atoms on the ring skeleton, for example, a substituent J as defined herein.

In one embodiment, R4, R5, R6, R7, R15, R16, and R17 are, independently, the same or different, and are selected from hydrogen, alkyl, cycloalkyl, aryl, arylalkyl, alkylaryl, heterocyclic, heteroaryl, alkenyl, alkynyl, halo (F, Cl, Br, I), OR', N(R')$_2$, SR', OCOR', NHCOR', N(COR')COR', SCOR', OCOOR', and NHCOOR', wherein each R' is independently H, a lower alkyl ($C_1$-$C_6$), lower haloalkyl ($C_1$-$C_6$), lower alkoxy ($C_1$-$C_6$), lower alkenyl ($C_2$-$C_6$), lower alkynyl ($C_2$-$C_6$), lower cycloalkyl ($C_3$-$C_6$) aryl, heteroaryl, alkylaryl, or arylalkyl, wherein the groups can be substituted with one or more substituents as defined above).

Alternatively, one or more of R4 and R5, R5 and R6, R6 and R7, R15 and R16, and R16 and R17 together form a five, six, or seven-member ring, which ring can include one or more heteroatoms, such as O, S, and N (wherein N can be substituted with H or R').

The compounds of Formula H use the following numbering scheme for the various positions:

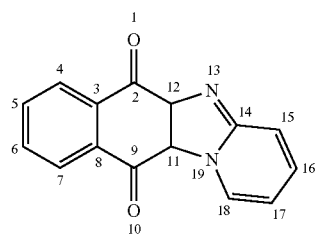

In one aspect of this embodiment, one or both of the nitrogens at positions 13 and 19 as listed above can be replaced with a CR' moiety.

Naphtho[2',3':4,5]imidazo[1,2-a]pyridine-6,11-dione is a representative compound of Formula H.

A similar structure to Formula H is shown below:

Formula H-A

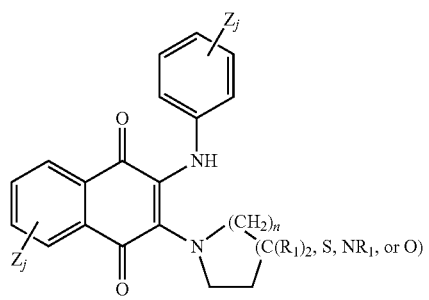

wherein n is 0, 1, or 2 and Z and j are as defined above.

Representative compounds are shown below:

Compound 95

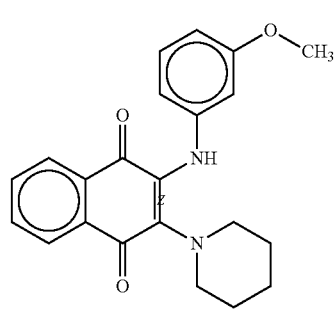

Compound 97

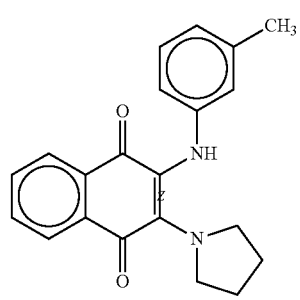

Compound 103

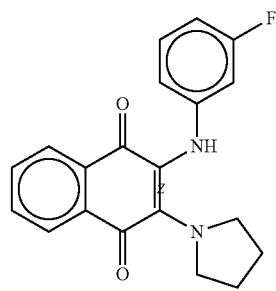

Compound 104

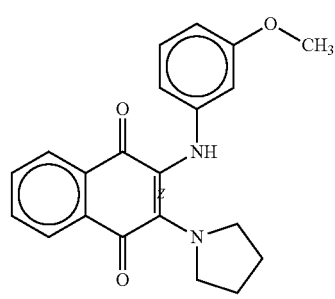

Compound 107

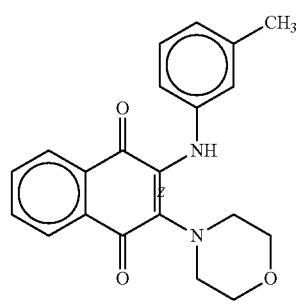

Compound 111
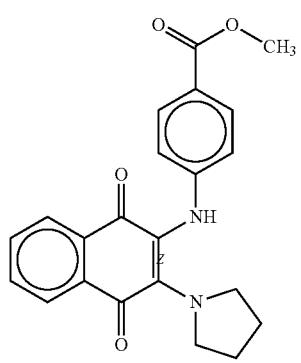
Compound 118
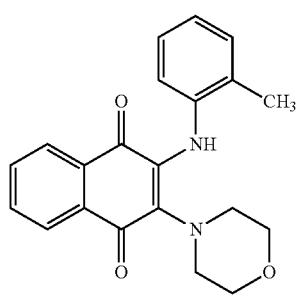
Compound 119
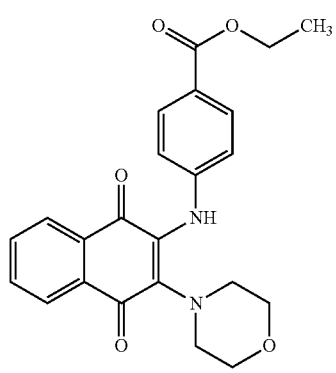
Compound 120
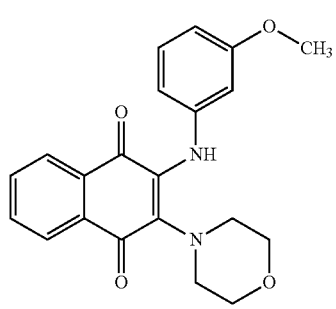
Compound 130
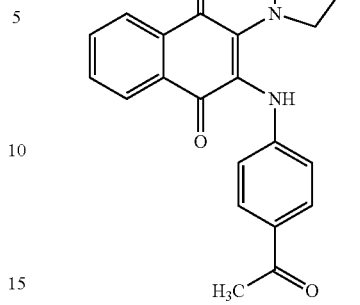
Compound 133
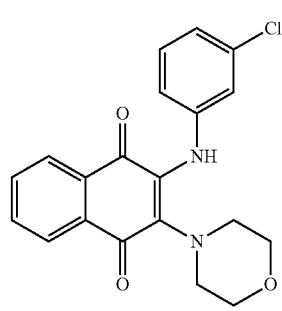
Compound 142
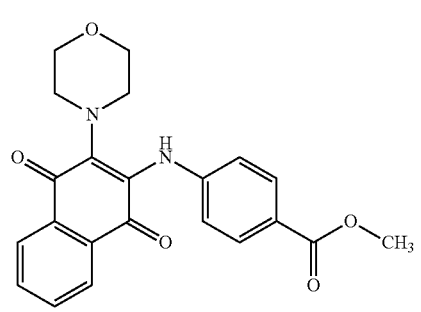
Compound 152
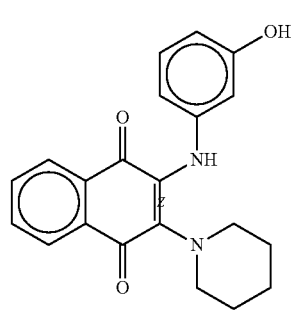
Compound 187
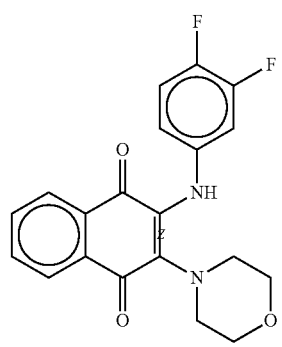

-continued

Compound 204
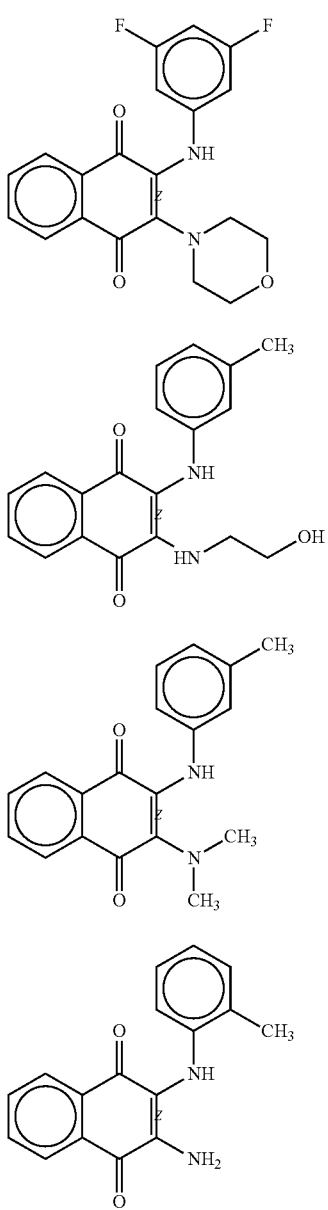

Compound 215

Compound 251

Compound 527

Additional anthraquinone-type compounds fall within the formula shown below:

Formula H-B
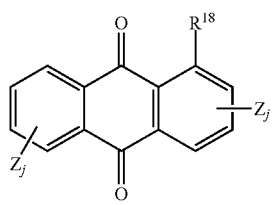

wherein $R^{18}$ is amine, including 4-8 membered ring azacycles (cyclic amines), and Z and j are as defined above. In one embodiment, the Z substituent on the ring with the $R^{18}$ moiety is H, alkyl, halo, or amine.

Representative compounds include the following:

Compound 96
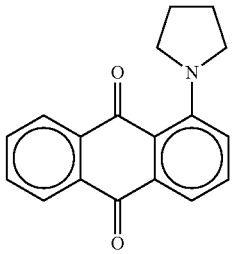

Compound 110
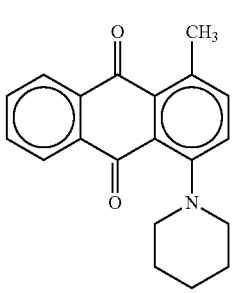

Compound 121
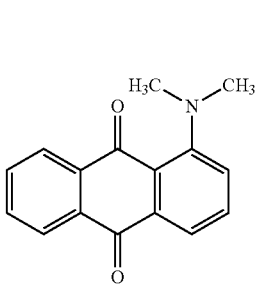

Compound 178
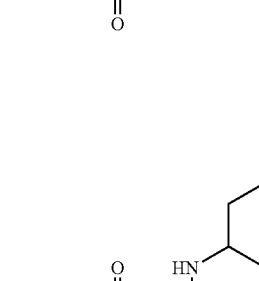

Compound 882
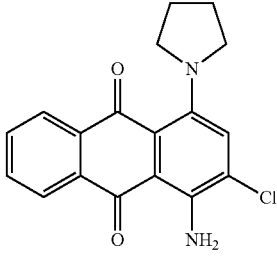

Still further anthraquinones have the following formula:

Formula H-C

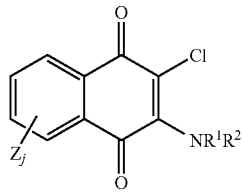

wherein Z, j, R$^1$ and R$^2$ are as defined above.
Representative compounds include the following:

Compound 156

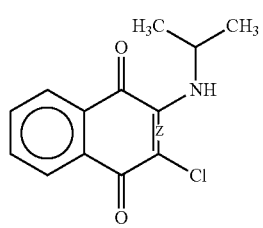

Compound 174

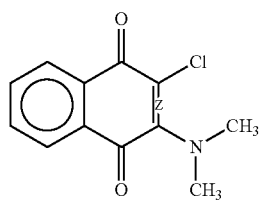

Compound 950

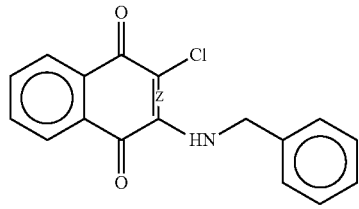

Formula I

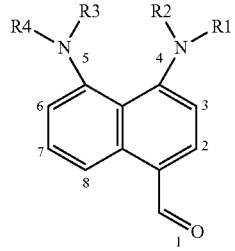

The analogs can have substantially any organic or inorganic substituent or functional group substituted in place of one or more of the hydrogen atoms on the ring skeleton (i.e., at positions 2, 3, 6, 7, and 8), for example, a substituent J as defined herein.

In one embodiment, these substituents are, independently, the same or different, and are selected from hydrogen, alkyl, cycloalkyl, aryl, arylalkyl, alkylaryl, heterocyclic, heteroaryl, alkenyl, alkynyl, halo (F, Cl, Br, I), OR', N(R')$_2$, SR', OCOR', NHCOR', N(COR')COR', SCOR', OCOOR', and NHCOOR', wherein each R' is independently H, a lower alkyl (C$_1$-C$_6$), lower haloalkyl (C$_1$-C$_6$), lower alkoxy (C$_1$-C$_6$), lower alkenyl (C$_2$-C$_6$), lower alkynyl (C$_2$-C$_6$), lower cycloalkyl (C$_3$-C$_6$) aryl, heteroaryl, alkylaryl, or arylalkyl, wherein the groups can be substituted with one or more substituents as defined above).

R1, R2, R3, and R4, are independently, the same or different, and are selected from hydrogen, alkyl, cycloalkyl, aryl, arylalkyl, alkylaryl, heterocyclic, heteroaryl, alkenyl, alkynyl, —COR', and —COOR', wherein R' is, independently H, a lower alkyl (C$_1$-C$_6$), lower haloalkyl (C$_1$-C$_6$), lower alkoxy (C$_1$-C$_6$), lower alkenyl (C$_2$-C$_6$), lower alkynyl (C$_2$-C$_6$), lower cycloalkyl (C$_3$-C$_6$) aryl, heteroaryl, alkylaryl, or arylalkyl, wherein the groups can be substituted with one or more substituents as defined above).

In one embodiment, one or both of R1 and R2, and R3 and R4, together with the nitrogens to which they are attached, form a 5-7 membered ring, which can include one or more additional heteroatoms such as O, S, or N, wherein the N can be bonded to a substituent R', as defined above).

4,5-Bis(dimethylamino)-1-naphthaldehyde (Compound 10) is a representative compound of Formula I.

Formula J

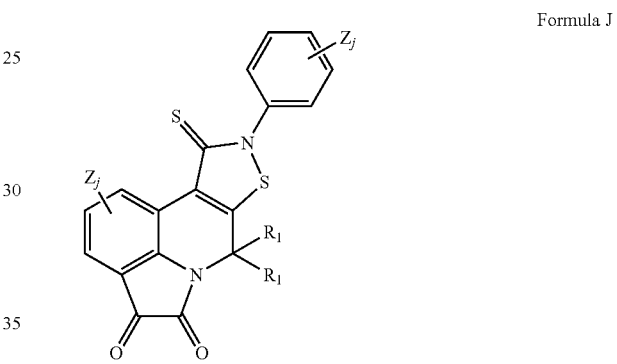

Formula K

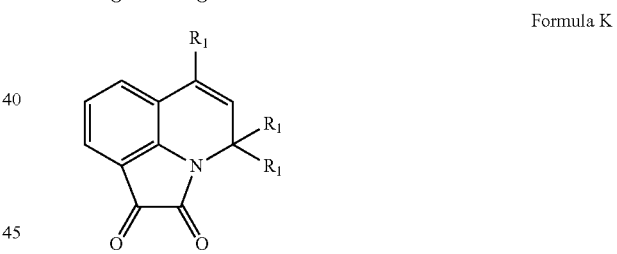

Formula L

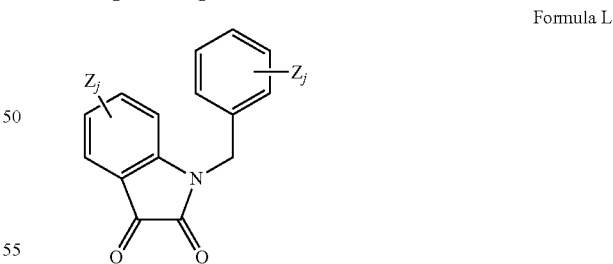

wherein, for compounds of Formulas J, K, and L, R$_1$, Z and j are as defined above. In a specific embodiment of Formulas J and K, both of R$_1$ adjacent the ring nitrogen are methyl. In another embodiment, both of these R$_1$ moieties link together to form a five, six, or seven-membered ring, which can optionally include a heteroatom such as O, S, or N. Compounds 14, 18, 22, and 24 are specific examples of Formula J. Compounds 23, 34, 35, 68, 82, and 85 are specific examples of Formula K. Compounds 30, 67, 78, and 103 are specific examples of Formula L.

Formula M

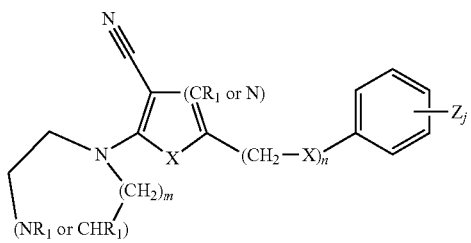

wherein X, Z, j, m and $R_1$ are as defined above.

In a specific embodiment, X in the heteroaryl ring is O and/or X in the bridge between the aryl and heteroaryl ring is O. In one embodiment, n is 0, and in another embodiment, n is 1. Compounds 84 and 101 are specific examples of Formula M, where n is 1. Compounds 63, 89, and 113 are specific examples of Formula M, where n is 0. Examples of heterocyclic rings that can be attached to the heteroaryl ring include piperidine, piperazine, azacycloheptane, azacyclohexane, azacyclopentane, and morpholine.

Formula N

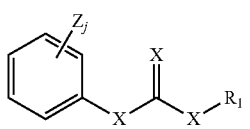

wherein X, Z, j, are as defined above.

A specific subset of the compounds of Formula N have the following formula:

Formula N-I

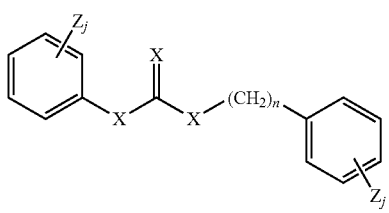

That is, these compounds fall within the definition of Formula N, where $R_1$ is alkaryl or aryl. In a specific embodiment, the X variables are selected so as to form a thiourea moiety. In another specific embodiment, at least one Z substituent is present on at least one aryl ring, and the substituent is an $-NH_2$, primary or secondary amine group. Compounds 76, 94, and 110 are specific examples of Formula M where n is 0. Compounds 41 and 55 are specific examples of Formula N where n is 1.

Other compounds falling generally into the definition of Formula N, where $R_1$ is alkyl (in one case, cyclohexyl, a cycloalkyl moiety), include compounds 71 and 109.

Formula O

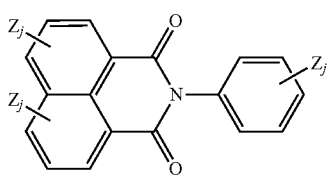

wherein X, Z, j, and m are as defined above. In a specific embodiment, at least one aryl ring includes a nitro group. Compounds 54 and 93 are specific examples of Formula M.

Formula P

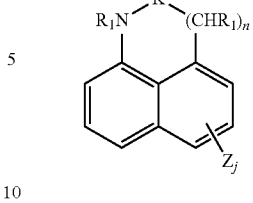

wherein Z, j, n, and $R_1$ are as defined above, and a) K is $NR_1$, or b) K is $N(R_1)_2$, and the link to the other ring nitrogen is absent, in which case the other $NR_1$ moiety is an $N(R_1)_2$ moiety rather than an $NR_1$ moiety.

Specific compounds within the scope of Formula P include compounds 1 and 10.

Formula Q

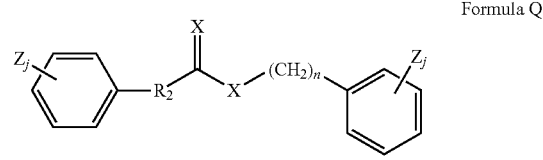

wherein Z, j, n, and X are as defined above, and $R_2$ is absent (i.e., a direct link between the aryl ring and the C=X moiety), or is an alkyl or cycloalkyl moiety linking the aryl ring and the C=X moiety. Compounds 97, 104, 106, and 108 are examples of specific compounds falling within Formula Q.

Formula R

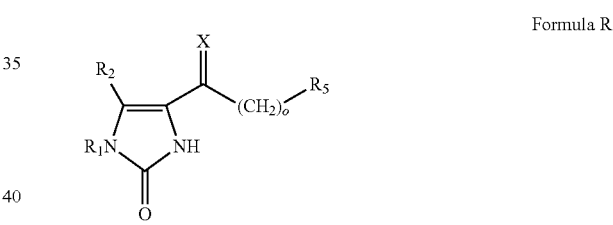

wherein X and $R_1$ are as defined elsewhere herein, o is an integer from 4 to 8 (in compounds 2 and 3, the number is 5), $R_2$ is $C_{1-6}$ alkyl, and $R_5$ is $-C(=X)OR_1$, $-C(=X)SR_1$, $-C(=X)NHR_1$, $-X-C(=X)OR_1$, $-X-C(=X)SR_1$, $-X-C(=X)NHR_1$, $-O-R_1$, $-SR_1$, or $-NHR_1$. In one embodiment, where the ring nitrogen is bound to $R_1$, the $NR_1$ is an amide moiety, and the amide moiety functions as a prodrug form of compounds in which the NR1 is an amine.

Formula S

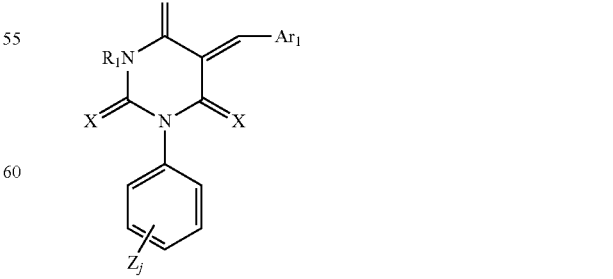

wherein X is O or S, and Z, j, $R_1$, and $Ar_1$ are as defined above.

Representative compounds of Formula S are shown below:
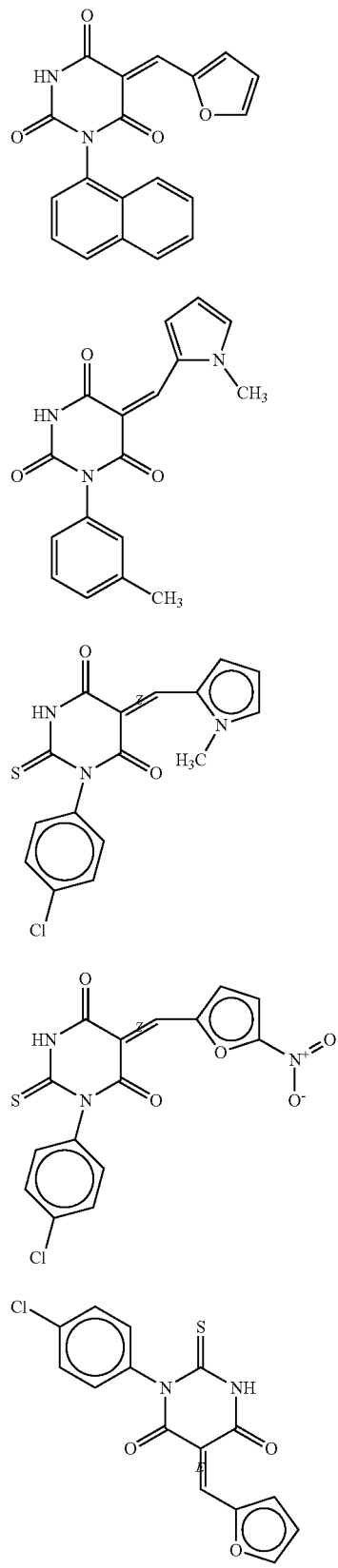
Compound 137
Compound 149
Compound 224
Compound 257
Compound 261
-continued
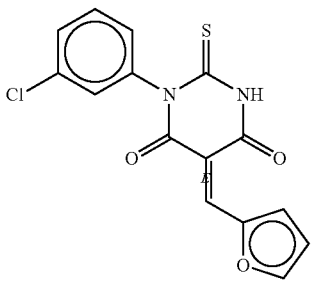
Compound 322
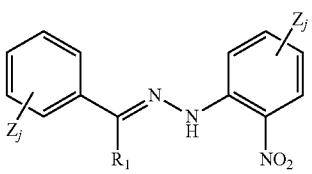
Formula T
wherein $R_1$, Z, and j are as defined above.
Representative compounds of Formula T are shown below:
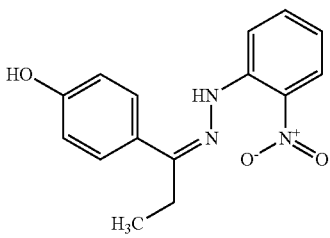
Compound 168
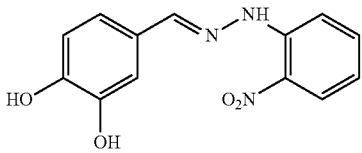
Compound 186
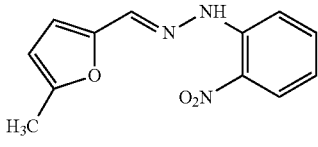
Compound 252
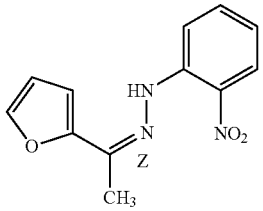
Compound 268
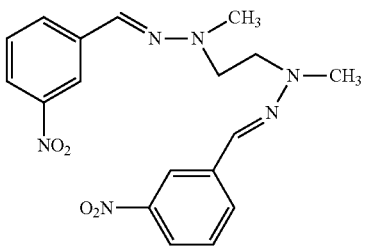
Compound 451

-continued

Formula U

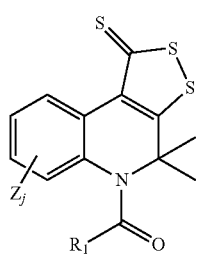

Formula U-1

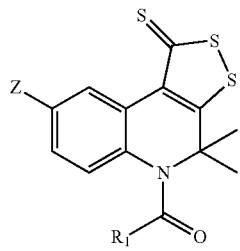

wherein Z and $R_1$ are as defined above. In one embodiment, Z is $C_{1-6}$ alkyl or O—$C_{1-6}$alkyl.

Representative compounds of Formula U and U-I are provided below:

Compound 185

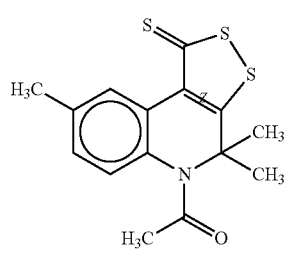

Compound 197

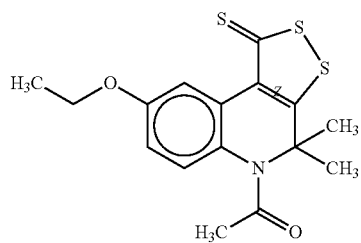

Compound 238

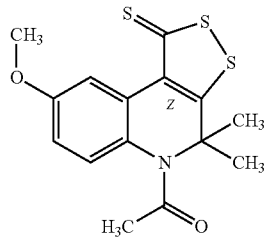

Formula V

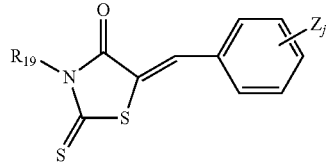

wherein $R_{19}$ is NHC(O)$Ar_1$, and Z and j are as defined above.

Representative compounds of Formula V are shown below:

Compound 199

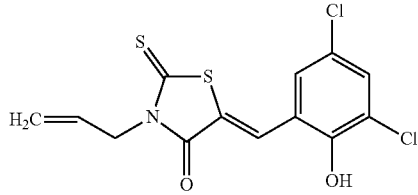

Compound 275

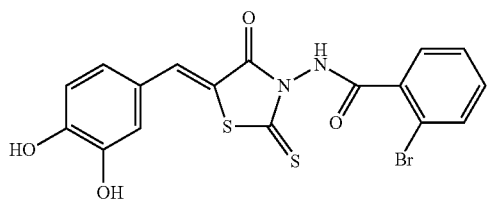

Compound 292

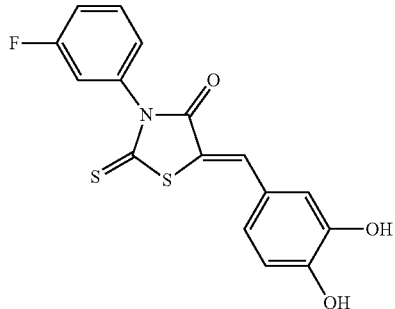

Compound 300

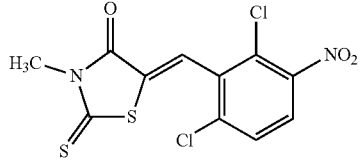

Compound 309

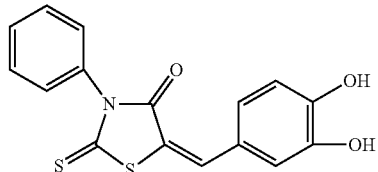

Compound 365

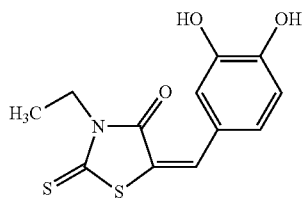

Compound 386

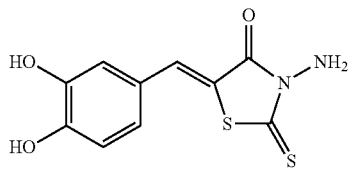

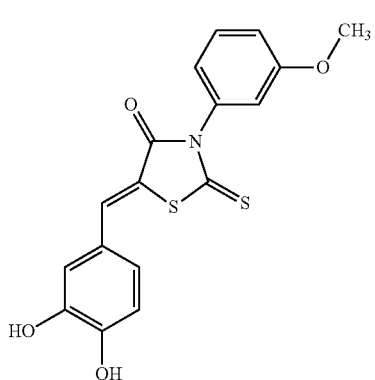

Compound 716

Compounds 8, 32, 40, 57, 75, 83, 95, and 114 do not fall within the scope of the various Formulas A through R. These compounds were also active, and compounds of these formulas, where the aryl or heteroaryl rings can be substituted with from one to three Z substituents are also within the scope of the invention.

A number of compounds appear active in the assays described herein, and are all highly conjugated molecules. These compounds include Compounds 7, 26, 38, 46, 47, 59, 65, 72, 86, 92, and 102. These compounds are generally types of compounds known to be highly conjugated, including benzophenones, triarylmethanes, fulvenes, and the like.

In each of these compounds, particularly those of Formula Q, an ester group can be replaced with an amide or thioamide moiety to increase the in vivo stability. Carbamate, thiocarbamate, urea, thiourea, ether, and thioether moieties can also be substituted for ester moieties. Aryl rings can be replaced with heteroaryl rings, such as thiophene rings in any of these compounds. For example, Compound 143 is an example of a compound that would fall within Formula Q if one of the aryl rings is replaced with a thiophene ring, n is 0, and $R_2$ is a direct link between the aryl ring and the C=X moiety. All of the compounds can optionally be substituted with a morpholinyl or piperidinyl moiety, which can be desirable to increase hydrophilicity.

In one embodiment, compounds of Formulas H and I are intended to be specifically excluded.

Novel compounds may also be formed in a combination of substituents which creates a chiral center or another form of an isomeric center. In this embodiment, the compound may exist as a racemic mixture, a pure enantiomer, and any enantiomerically enriched mixture.

The compounds can occur in varying degrees of enantiomeric excess, and racemic mixtures can be purified using known chiral separation techniques.

The compounds can be in a free base form or in a salt form (e.g., as pharmaceutically acceptable salts). Examples of suitable pharmaceutically acceptable salts include inorganic acid addition salts such as sulfate, phosphate, and nitrate; organic acid addition salts such as acetate, dichloroacetate, galactarate, propionate, succinate, lactate, glycolate, malate, tartrate, citrate, maleate, fumarate, methanesulfonate, p-toluenesulfonate, and ascorbate; salts with an acidic amino acid such as aspartate and glutamate; alkali metal salts such as sodium and potassium; alkaline earth metal salts such as magnesium and calcium; ammonium salt; organic basic salts such as trimethylamine, triethylamine, pyridine, picoline, dicyclohexylamine, and N,N'-dibenzylethylenediamine; and salts with a basic amino acid such as lysine and arginine. The salts can be in some cases hydrates or ethanol solvates. The stoichiometry of the salt will vary with the nature of the components.

Representative compounds include the following: 3-ethyl-6-methoxy-1H-benzo[de]cinnoline, methyl 6-(5-methyl-2-oxo-2,3-dihydro-1H-imidazol-4-yl)-6-oxohexanoate, ethyl 6-(1-benzoyl-5-methyl-2-oxo-2,3-dihydro-1H-imidazol-4-yl)-6-oxohexanoate, 2-[(8-ethoxy-4-methyl-2-quinazolinyl)amino]-5,6,7,8-tetrahydro-4(1H)-quinazolinone, 2-[(6-methoxy-4-methyl-2-quinazolinyl)amino]-5,6-dimethyl-4(1H)-pyrimidinone, 2-[(4,7-dimethyl-2-quinazolinyl)amino]-6-propyl-4(3H)-pyrimidinone, tris[4-(dimethylamino)phenyl]methanol, 5-(2-oxohexahydro-1H-thieno[3,4-d]imidazol-4-yl)pentanoic acid, N-ethyl-5-nitro-N-phenyl-2,1,3-benzoxadiazol-4-amine, 4,5-bis(dimethylamino)-1-naphthaldehyde, N,N-dimethyl-N'-[4-(2-pyridinyl)-1,3-thiazol-2-yl]-1,4-benzenediamine hydrobromide, N~2~-(4,6-dimethyl-2-pyrimidinyl)-2,4-quinazolinediamine hydrochloride, 2-[(4,6,7-trimethyl-2-quinazolinyl)amino]-5,6,7,8-tetrahydro-4(1H)-quinazolinone, 9-(2-methoxyphenyl)-2,3,7,7-tetramethyl-10-thioxo-9,10-dihydro-7H-isothiazolo[5,4-c]pyrrolo[3,2,1-ij]quinoline-4,5-dione, 2-[(4,8-dimethyl-2-quinazolinyl)amino]-5,6,7,8-tetrahydro-4(1H)-quinazolinone, 2-[(4-methyl-2-quinazolinyl)amino]-6-propyl-4(1H)-pyrimidinone, 2-[(4-acetylphenyl)amino]-3-(1-pyrrolidinyl)naphthoquinone, 9-(2,5-dimethoxyphenyl)-2-methoxy-7,7-dimethyl-10-thioxo-9,10-dihydro-7H-isothiazolo[5,4-c]pyrrolo[3,2,1-ij]quinoline-4,5-dione, [3-(1,3-benzodioxol-5-yl)-3-phenylpropyl][4-(dimethylamino)benzyl]amine hydrochloride, 2-[(4,7-dimethyl-2-quinazolinyl)amino]-5-ethyl-6-methyl-4(3H)-pyrimidinone, N-[2-(1-cyclohexen-1-yl)ethyl]-2-(3-methylphenyl)-5-nitro-2H-1,2,3-triazol-4-amine 3-oxide, 2-methoxy-7,7-dimethyl-9-(2-propoxyphenyl)-10-thioxo-9,10-dihydro-7H-isothiazolo[5,4-c]pyrrolo[3,2,1-ij]quinoline-4,5-dione, 4,4,6-trimethyl-1,2-dioxo-1,2-dihydro-4H-pyrrolo[3,2,1-ij]quinolin-8-yl 2-methylbenzoate, 9-(2,3-dimethylphenyl)-2-methoxy-7,7-dimethyl-10-thioxo-9,10-dihydro-7H-isothiazolo[5,4-c]pyrrolo[3,2,1-ij]quinoline-4,5-dione, N'-(2-methoxybenzyl)-N,N-dimethyl-1,4-benzenediamine, 2-(4-ethylphenyl)naphthoquinone, 2-[(4,6-dimethyl-2-quinazolinyl)amino]-1,5,6,7-tetrahydro-4H-cyclopenta[d]pyrimidin-4-one, 5-nitro-4-(1-piperidinyl)-2,1,3-benzoxadiazole, N,N-dimethyl-N'-[2-nitro-4-(trifluoromethyl)phenyl]-1,3-benzenediamine, 1-[2-(benzyloxy)benzyl]-5-methyl-1H-indole-2,3-dione, 1-[2-chloro-4-nitro-5-(vinylthio)-3-thienyl]pyrrolidine, 2-(4-ethylphenyl)-5-methyl-4-[4-(4-morpholinyl)benzylidene]-2,4-dihydro-3H-pyrazol-3-one, (2-methoxybenzyl)[4-(1-piperidinyl)phenyl]amine, 4,4,6-trimethyl-1,2-dioxo-1,2-dihydro-4H-pyrrolo[3,2,1-ij]quinolin-8-yl 2-methoxybenzoate, 4,4,6-trimethyl-1,2-dioxo-1,2-dihydro-4H-pyrrolo[3,2,1-ij]quinolin-8-yl 2-chlorobenzoate, 4-({[3-(2-furyl)-3-(2-methoxyphenyl)propyl]amino}methyl)-N,N-dimethylaniline, N'-[4-(allyloxy)-3-chloro-5-methoxybenzyl]-N,N-dimethyl-1,4-benzenediamine, 2,6,7-trihydroxy-9-(5-nitro-2-furyl)-3H-xanthen-3-one, 2-[ethyl(4-{[2-nitro-4-(trifluoromethyl)phenyl]amino}phenyl)amino]ethanol, 5-[4-(dimethylamino)phenyl]-3-(4-methoxyphenyl)-N-methyl-4,5-dihydro-1H-pyrazole-1-carbothioamide, N-[4-(dimethylamino)phenyl]-N'-(4-methylbenzyl)thiourea, N-[4-(allyloxy)-3-methoxybenzyl]-4-(1-pyrrolidinyl)aniline, 5-methyl-N-[7-(4-morpholinyl)-2,1,3-benzoxadiazol-4-yl]-4-phenyl-3-thiophenecarboxamide, 4-[2-chloro-4-nitro-5-(vinylthio)-3-thienyl]morpholine, 1-(4-fluorophenyl)-2-(2-nitrovinyl)-1H-pyrrole, 1,1'-(2,4-cyclopentadien-1-ylidenemethylene)

bis(4-methoxybenzene), 3-(2-chlorophenyl)-6-ethyl-7-methoxy-4H-chromene-4-thione, N-[4-hydroxy-3-(phenylthio)-1-naphthyl]-4-methoxybenzenesulfonamide, 1-(4-chlorophenyl)-2-(2-nitrovinyl)-1H-pyrrole, 4-({[3-(2-furyl)-4-phenylbutyl]amino}methyl)-N,N-dimethylaniline, 4-(4-benzyl-1-piperazinyl)-N-(4-fluorobenzyl)aniline; (2-ethoxy-3-methoxybenzyl)[4-(1-pyrrolidinyl)phenyl]amine, (4-fluorobenzyl)[4-(1-pyrrolidinyl)phenyl]amine, 6-(dimethylamino)-2-(2-methylphenyl)-5-nitro-1H-benzo[de]isoquinoline-1,3(2H)-dione, N-(4-chlorobenzyl)-N'-[4-(diethylamino)phenyl]thiourea, 4-fluoro-N-[4-hydroxy-3-(phenylthio)-1-naphthyl]benzenesulfonamide, 2-bicyclo[2.2.1]hept-2-yl-5-nitro-1H-isoindole-1,3(2H)-dione, N-[2-(1H-indol-3-yl)ethyl]-9-acridinamine, 6-bromo-2-(3-methoxy-4-propoxyphenyl)-3-nitro-2H-chromene, ethyl 3-(4-methoxyphenyl)-1,4-dioxo-1,4-dihydro-2-naphthalenecarboxylate, (2-methoxyphenyl)[2-nitro-4-(trifluoromethyl)phenyl]amine, N'-(2,8-dimethyl-4-quinolinyl)-N,N-dimethyl-1,4-benzenediamine hydrochloride, 2-(2-methylphenyl)-5-(1-piperidinyl)-1,3-oxazole-4-carbonitrile, N-[4-hydroxy-3-(phenylthio)-1-naphthyl]benzenesulfonamide, 1-(4-chlorophenyl)-5-[(5-nitro-2-furyl)methylene]-2,4,6(1H,3H,5H)-pyrimidinetrione, N'-(4,6-dimethyl-2-pyrimidinyl)-N,N-dimethyl-1,4-benzenediamine, 5-bromo-1-(2-chlorobenzyl)-1H-indole-2,3-dione, 4,4,6-trimethyl-1,2-dioxo-1,2-dihydro-4H-pyrrolo[3,2,1-ij]quinolin-8-yl 2-thiophenecarboxylate, 2-({[4-(dimethylamino)phenyl]amino}methyl)phenol, 2-(2-fluorophenyl)-3-(1-methyl-1H-pyrrol-2-yl)acrylonitrile, N-[4-(diethylamino)phenyl]-N'-isobutylthiourea, 2-(4-ethylphenyl)-4-(4-hydroxy-3,5-dimethoxybenzylidene)-5-methyl-2,4-dihydro-3H-pyrazol-3-one, N-(2-methoxyphenyl)-3-nitro-2-pyridinamine, ethyl 3-(4-methylphenyl)-1,4-dioxo-1,4-dihydro-2-naphthalenecarboxylate, 5-{[(2-nitrophenyl)thio]amino}-1,3-benzodioxole, N-[4-(diethylamino)phenyl]-N'-(4-ethoxyphenyl)thiourea, N-[4-hydroxy-3-(phenylthio)-1-naphthyl]-2-thiophenesulfonamide, 1-benzyl-5-bromo-7-methyl-1H-indole-2,3-dione, N-[4-(dimethylamino)benzyl]-6-methyl-2-pyridinamine, 2-[2-bromo-4-({[4-(dimethylamino)phenyl]amino}methyl)-6-ethoxyphenoxy]-Nert-butyl) acetamide, N-[4-(dimethylamino)benzyl]-1-pentyl-1H-benzimidazol-2-amine, 4,6-diethyl-4,8-dimethyl-4H-pyrrolo[3,2,1-ij]quinoline-1,2-dione, N-[(1-methyl-1H-pyrrol-2-yl)methylene]-4-(1-naphthylmethyl)-1-piperazinamine, 5-(1-azepanyl)-2-[(3-chlorophenoxy)methyl]-1,3-oxazole-4-carbonitrile, 6'-methyl-5',6'-dihydrospiro[cyclohexane-1,4'-pyrrolo[3,2,1-ij]quinoline]-1',2'-dione, 4-(di-1H-indol-3-ylmethyl)-1,2-benzenediol, (5-bromo-2-methoxybenzyl)[4-(4-morpholinyl)phenyl]amine, 1-[2-chloro-4-nitro-5-(vinylthio)-3-thienyl]piperidine, 5-(1-azepanyl)-2-(2-fluorophenyl)-1,3-oxazole-4-carbonitrile, 4-(2-{[4-(diethylamino)phenyl]amino}-1,3-thiazol-4-yl)-1,2-benzenediol, 1-butyl-N-[4-(diethylamino)benzyl]-1H-benzimidazol-2-amine, (4-bromophenyl)[3-nitro-4-(1-piperidinyl)phenyl]methanone, 2-(2,5-dimethylphenyl)-6-nitro-1H-benzo[de]isoquinoline-1,3(2H)-dione, N-[4-(diethylamino)phenyl]-N'-(2,4-dimethoxyphenyl)thiourea, 5-(dimethylamino)-1,3-benzothiazole-2-thiol, ethyl 3-(4-ethylbenzyl)-1,4-dioxo-1,4-dihydro-2-naphthalenecarboxylate, 4-propylphenyl 4-nitrobenzoate, 4-({[3-(2-furyl)-3-(4-methylphenyl)propyl]amino}methyl)-N,N-dimethylaniline, N-benzyl-5-(4-benzyl-1-piperazinyl)-2-nitroaniline, N-benzyl-4-chloro-2-nitroaniline, 5-(1-azepanyl)-2-[(4-chlorophenoxy)methyl]-1,3-oxazole-4-carbonitrile, [4-(2,6-dimethyl-4-morpholinyl)-3-nitrophenyl](4-ethoxyphenyl)methanone, 5-chloro-1-(2-chlorobenzyl)-1H-indole-2,3-dione, 2-fluorobenzyl 2-chloro-4-nitrobenzoate, 3-[(3,4-dimethylphenyl)amino]-1-(4-nitrophenyl)-1-propanone, N-[4-(diethylamino)phenyl]-2-phenylcyclopropanecarboxamide, 2-[2-bromo-6-methoxy-4-({[4-(1-pyrrolidinyl)phenyl]amino}methyl)phenoxy]acetamide, N-[4-(1-azepanyl)phenyl]-2-methylbenzamide, N-cyclohexyl-N'-[4-(dimethylamino)phenyl]thiourea, N-(3-chloro-4-fluorophenyl)-N'-[4-(diethylamino)phenyl]thiourea, 4,6-dimethyl-N-[4-(1-pyrrolidinyl)phenyl]-2-pyrimidinamine, (2,6-dichlorobenzyl)[4-(1-pyrrolidinyl)phenyl]amine, 2-(2-fluorophenyl)-5-(4-phenyl-1-piperazinyl)-1,3-oxazole-4-carbonitrile, and 1-[4-nitro-3-(1-pyrrolidinyl)phenyl]-4-(2-thienylcarbonyl)piperazine.

Specific compounds also include N-{4-methyl-5-[(pentan-3-yl)carbamoyl]thiophen-2-yl}furan-2-carboxamide, 2-[3-ethyl-4-oxo-5-(thiophen-3-ylmethylidene)-1,3-thiazolidin-2-ylidene]propanedinitrile, 2-[(4-cyclopropyl-5-oxo-4,5-dihydro-1H-1,2,4-triazol-3-yl)sulfanyl]-N,N-bis(propan-2-yl)propanamide, N-(cyclohexylmethyl)-3-[5,7-dimethyl-2-(trifluoromethyl)-[1,2,4]triazolo[1,5-a]pyrimidin-6-yl]propanamide, 4-{4-[2,5-dimethyl-1-(1,2-oxazol-3-yl)-1H-pyrrol-3-yl]-1,3-thiazol-2-yl}-2,5,6-trimethyl-2,3-dihydropyridazin-3-one, 2-methyl-N-(3-nitropyridin-2-yl)-1H-indol-5-amine, 2-[(pyrimidin-2-ylsulfanyl)methyl]quinazolin-4-amine Potential R-Group Substitutions:

Novel compounds may also be formed in the event that some combination of substituents creates a chiral center or another form of an isomeric center in any compound of the present list. The list would include any or all of the racemic mixture, pure enantiomers, and any enantiomerically enriched mixture.

For example, in one embodiment, the amino groups at the 4 and/or 5 position on the naphthalene ring in the compounds of formula I can be replaced with —C($R_1$)$_3$, —O$R_1$, or —S$R_1$.

Representative compounds include the following:
4,5-bis(dimethylamino)-1-naphthaldehyde
4,5-bis(diethylamino)-1-naphthaldehyde
4,5-bis(dipropylamino)-1-naphthaldehyde
4,5-bis(dibutylamino)-1-naphthaldehyde
4,5-bis(methylethylamino)-1-naphthaldehyde
4,5-bis(methylpropylamino)-1-naphthaldehyde
4,5-bis(methylbutylamino)-1-naphthaldehyde
4,5-bis(ethylpropylamino)-1-naphthaldehyde
4,5-bis(ethylbutylamino)-1-naphthaldehyde
4,5-bis(dimethylamino)-1-naphthaldehyde
4,5-bis(dimethylamino)-1-naphthaldehyde
4,5-bis(dimethylamino)-1-naphthaldehyde
4,5-bis(dimethylamino)-1-naphthaldehyde
4,5-bis(dimethylamino)-1-naphthaldehyde
4,5-bis(dimethylamino)-1-naphthaldehyde
4,5-bis(dimethylamino)-1-naphthaldehyde
4,5-bis(dimethylamino)-1-naphthaldehyde
4,5-bis(dimethylamino)-1-naphthaldehyde
4,5-bis(dimethylamino)-1-naphthaldehyde
4,5-bis(dimethylamino)-1-naphthaldehyde
4,5-bis(dimethylamino)-1-naphthaldehyde
4,5-bis(dimethylamino)-1-naphthaldehyde
4,5-bis(dimethylamino)-1-naphthaldehyde
4,5-bis(dimethylamino)-1-naphthaldehyde
4,5-bis(dimethylamino)-1-naphthaldehyde
4,5-bis(dimethylamino)-1-naphthaldehyde
4,5-bis(dimethylamino)-1-naphthaldehyde 4,5-bis(dimethylamino)-1-naphthaldehyde
4,5-bis(dimethylamino)-1-naphthaldehyde
4,5-bis(dimethylamino)-1-naphthaldehyde
4,5-bis(dimethylamino)-1-naphthaldehyde
4,5-bis(dimethylamino)-1-naphthaldehyde
4,5-bis(dimethylamino)-1-naphthaldehyde
4,5-bis(dimethylamino)-1-naphthaldehyde
4,5-bis(dimethylamino)-1-naphthaldehyde
4,5-bis(dimethylamino)-1-naphthaldehyde
4,5-bis(dimethylamino)-1-naphthaldehyde
4-dimethylamino-5-diethylamino-1-naphthaldehyde
4-dimethylamino-5-dipropylamino-1-naphthaldehyde
4-dimethylamino-5-dibutylamino-1-naphthaldehyde
4-diethylamino-5-dimethylamino-1-naphthaldehyde
4-diethylamino-5-dipropylamino-1-naphthaldehyde
4-diethylamino-5-dibutylamino-1-naphthaldehyde
4-dipropylamino-5-dimethylamino-1-naphthaldehyde
4-dipropylamino-5-diethylamino-1-naphthaldehyde
4-dipropylamino-5-dibutylamino-1-naphthaldehyde.

II. Synthetic Methods

The compounds described herein all include at least one aryl or heteroaryl ring, and all of these rings can be further substituted with one or more substituents, as defined herein. Those skilled in the art will readily understand that incorporation of other substituents onto an aryl or heteroaryl ring used as a starting material to prepare the compounds described herein, and other positions in the compound framework, can be readily realized. Such substituents can provide useful properties in and of themselves or serve as a handle for further synthetic elaboration.

Benzene rings (and pyridine, pyrimidine, pyrazine, and other heteroaryl rings) can be substituted using known chemistry, including the reactions discussed below. For example, the nitro group on nitrobenzene can be reacted with sodium nitrite to form the diazonium salt, and the diazonium salt manipulated as discussed above to form the various substituents on a benzene ring.

Diazonium salts can be halogenated using various known procedures, which vary depending on the particular halogen. Examples of suitable reagents include bromine/water in concentrated HBr, thionyl chloride, pyr-ICl, fluorine and Amberlyst-A A number of other analogs, bearing substituents in the diazotized position, can be synthesized from the corresponding amino compounds, via the diazocyclopentadiene intermediate. The diazo compounds can be prepared using known chemistry, for example, as described above.

The nitro derivatives can be reduced to the amine compound by reaction with a nitrite salt, typically in the presence of an acid. Other substituted analogs can be produced from diazonium salt intermediates, including, but are not limited to, hydroxy, alkoxy, fluoro, chloro, iodo, cyano, and mercapto, using general techniques known to those of skill in the art.

For example, hydroxy-aromatic/heteroaromatic analogues can be prepared by reacting the diazonium salt intermediate with water. Halogens on an aryl or heteroaryl ring can be converted to Grignard or organolithium reagents, which in turn can be reacted with suitable aldehyde or ketone to form alcohol-containing side chains. Likewise, alkoxy analogues can be made by reacting the diazo compounds with alcohols. The diazo compounds can also be used to synthesize cyano or halo compounds, as will be known to those skilled in the art. Mercapto substitutions can be obtained using techniques described in Hoffman et al., *J. Med. Chem.* 36: 953 (1993). The mercaptan so generated can, in turn, be converted to an alkylthio substitutent by reaction with sodium hydride and an appropriate alkyl bromide. Subsequent oxidation would then provide a sulfone. Acylamido analogs of the aforementioned compounds can be prepared by reacting the corresponding amino compounds with an appropriate acid anhydride or acid chloride using techniques known to those skilled in the art of organic synthesis.

Hydroxy-substituted analogs can be used to prepare corresponding alkanoyloxy-substituted compounds by reaction with the appropriate acid, acid chloride, or acid anhydride. Likewise, the hydroxy compounds are precursors of both the aryloxy and heteroaryloxy via nucleophilic aromatic substitution at electron deficient aromatic rings. Such chemistry is well known to those skilled in the art of organic synthesis. Ether derivatives can also be prepared from the hydroxy compounds by alkylation with alkyl halides and a suitable base or via Mitsunobu chemistry, in which a trialkyl- or triarylphosphine and diethyl azodicarboxylate are typically used. See Hughes, *Org. React.* (N.Y.) 42: 335 (1992) and Hughes, *Org. Prep. Proced. Int* 28: 127 (1996) for typical Mitsunobu conditions.

Cyano-substituted analogs can be hydrolyzed to afford the corresponding carboxamido-substituted compounds. Further hydrolysis results in formation of the corresponding carboxylic acid-substituted analogs. Reduction of the cyano-substituted analogs with lithium aluminum hydride yields the corresponding aminomethyl analogs. Acyl-substituted analogs can be prepared from corresponding carboxylic acid-substituted analogs by reaction with an appropriate alkyllithium using techniques known to those skilled in the art of organic synthesis.

Carboxylic acid-substituted analogs can be converted to the corresponding esters by reaction with an appropriate alcohol and acid catalyst. Compounds with an ester group can be reduced with sodium borohydride or lithium aluminum hydride to produce the corresponding hydroxymethyl-substituted analogs. These analogs in turn can be converted to compounds bearing an ether moiety by reaction with sodium hydride and an appropriate alkyl halide, using conventional techniques. Alternatively, the hydroxymethyl-substituted analogs can be reacted with tosyl chloride to provide the corresponding tosyloxymethyl analogs, which can be converted to the corresponding alkylaminoacyl analogs by sequential treatment with thionyl chloride and an appropriate alkylamine. Certain of these amides are known to readily undergo nucleophilic acyl substitution to produce ketones.

Hydroxy-substituted analogs can be used to prepare N-alkyl- or N-arylcarbamoyloxy-substituted compounds by reaction with N-alkyl- or N-arylisocyanates. Amino-substituted analogs can be used to prepare alkoxycarboxamido-substituted compounds and urea derivatives by reaction with alkyl chloroformate esters and N-alkyl- or N-arylisocyanates, respectively, using techniques known to those skilled in the art of organic synthesis.

Synthesis of Compounds of Formula A

The compounds of Formula A include an aryl or heteroaryl ring linked to another aryl or heteroaryl ring to form an amine. Where $R_1$ is H, the compounds are secondary amines. Where $R_1$ is other than H, the compounds are tertiary amines. Where n is 0, the amine nitrogen is linked directly to the $Ar_1$ ring, and where n is 1, a methylene bridge exists between the amine nitrogen and the $Ar_1$ ring (i.e., a benzylamine when $Ar_1$ is a benzene ring). The formation of aniline moieties is well known, as discussed above with respect to forming amine substituents on aryl/heteroaryl rings. The formation of a benzylamine can take place by reacting a benzyl halide with an amine using standard nucleophilic displacement chemistry.

Synthesis of Compounds of Formula B

The compounds of Formula B include an aryl or heteroaryl ring linked to another aryl or heteroaryl ring to form an amine. Where $R_1$ is H, the compounds are secondary amines. Where $R_1$ is other than H, the compounds are tertiary amines. Where n is 0, the amine nitrogen is linked directly to the $Ar_1$ ring, and where n is 1, 2, or 3, an alkylene bridge exists between the amine nitrogen and the $Ar_1$ ring (i.e., a benzylamine, benzethylamine, and the like, when $Ar_1$ is a benzene ring). The formation of aniline moieties is well known, as discussed above with respect to forming amine substituents on aryl/heteroaryl rings. The formation of a benzylamine, benzethylamine, and the like can take place by reacting a arylalkyl halide with an amine using standard nucleophilic displacement chemistry.

Synthesis of Compounds of Formula C

The compounds of Formula C are 5-membered ring heteroaryl compounds which include various substituents at various positions on the rings. The nitro group at position 3 can be difficult to attach to an unsubstituted 5-membered ring heteroaryl, since the preference for nitration can be at the 2-position. However, once desired halo substituents are placed on 2 and 5 position on the ring, for example, by reacting the heteroaryl ring with an elemental halogen in the presence of acetic acid, the ring can be nitrated at the 3-position. The halogen at the 5-position can be reacted with vinyl sulfide in a nucleophilic displacement reaction to form the S-vinyl ether. A halogenation reaction will place a halogen at the 3-position, which can be displaced using a suitable amine to form the heterocyclic ring attached to the heteroaryl ring.

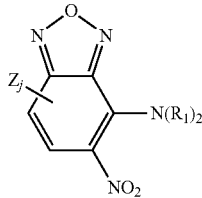

Formula D

Synthesis of Compounds of Formula D

The compounds of Formula D can be formed by starting with the unsubstituted ring structure, and performing a nitration reaction. Then, halogenation can be used to place a halogen at a position adjacent to the nitro group, and the halogen can be displaced with an amine to form the compounds of Formula D.

Synthesis of Compounds of Formula E

The compounds of Formula E include a haloaryl ring with a pyrrole ring attached para to the halogen. The pyrrole ring includes a $CH_2$=$CHNO_2$ moiety at the 2-position. This moiety can be provided, for example, by starting with a pyrrole with a CHO group at the 2-position, and using Wittig chemistry to attach the $CH_2$=$CHNO_2$ moiety. An aryl (i.e., phenyl) ring with a halogen at the 1-position and a diazonium salt at the 4-position can be reacted with the pyrrole to form a linkage between the pyrrole ring and the aryl ring.

Synthesis of Compounds of Formula F

The compounds of Formula F include a naphthyl ring that further includes an aryl sulfonamide moiety, an aryl thioether moiety, and an —OH or ether moiety. Starting from a naphthyl ring with appropriately positioned amine, thiol, and hydroxy groups, one can selectively protect two of the three groups. A thiol group can be reacted with a diazonium group on a benzene ring to form the aryl thioether. The amine group can be reacted with an aryl sulfonyl halide to form the sulfonamide moiety. The protected hydroxy group can be deprotected to form an OH group, which can then be converted to ethers or esters if desired, using known chemistry. Since an amine group is more nucleophilic than a hydroxy group, the sulfonamide can likely be prepared even in the presence of an unprotected hydroxy group.

Synthesis of Compounds of Formula G

The compounds of Formula G are napthoquinones. They can typically be prepared from appropriately substituted 1,4-quinones and dienes using Diels Alder chemistry (see, for example, Witayakron et al., Tetrahedron Letters, Volume 48, Issue 17, 23 Apr. 2007, Pages 2983-2987, the contents of which are hereby incorporated by reference).

Synthesis of Compounds of Formula H

The compounds of Formula H are also substituted napthoquinones. They can similarly be prepared from suitably appropriately substituted 1,4-quinones and dienes using Diels Alder chemistry. The quinones are prepared from 1,4-bisphenols, and the additional ring functionality can be incorporated by starting with 1,4-bisphenols with an amine group at the 2 position, and a pyridine carboxamide at the 3-position, where an imine linkage is formed between the carboxy group on the carboxamide and the amine at the 2-position.

Synthesis of Compounds of Formula I

The compounds of Formula I are naphthalenes with amines at the 4 and 5 position, and an aldehydes at the 1-position. Ideally, the amines are dialkylamines, so that they do not react with the aldehyde moiety to form an intramolecular imine group. Amine groups are typically formed on aromatic rings by a combination of nitration with nitric acid, and reduction of the nitro group to an amine group. Alkylation of the amine groups involves routine nucleophilic displacement chemistry with appropriate alkylamines, whereas arylation can involve reaction of an amine with a diazonium salt. The aldehydes moiety can be introduced by reacting an organolithium reagent (a naphthyl-lithium) with isonitriles to the corresponding lithium aldimine. Subsequent hydrolysis effectively converts the organolithium compound to its aldehydes (see, for example, G. E. Niznik, W. H. Morrison, III, and H. M. Walborsky (1988), "1-d-Aldehydes from Organometallic Reagents: 2-Methylbutanal-1-d", Org. Synth., Coll. Vol. 6: 751, the contents of which are hereby incorporated by reference).

Synthesis of Compounds of Formula J

The compounds of Formula J can be formed from appropriately functionalized dihydroquinolines. The amine in the dihydroquinoline can be reacted with oxaloyl chloride in a stepwise fashion, and the remaining acid chloride can be reacted with the aromatic ring via Friedel-Crafts acylation conditions to form the cyclic structure. From there, routine chemistry, for example, 3,2 Diels Alder chemistry heterocyclic ring structure, for example, by stepwise reaction of an aniline with appropriately functionalized groups on the dihydroquinoline framework.

Synthesis of Compounds of Formula K

The compounds of Formula K can be formed from appropriately functionalized dihydroquinolines. The amine in the dihydroquinoline can be reacted with oxaloyl chloride in a stepwise fashion, and the remaining acid chloride can be reacted with the aromatic ring via Friedel-Crafts acylation conditions to form the cyclic structure.

Synthesis of Compounds of Formula L

The compounds of Formula L can be formed from appropriately functionalized anilines. The amine in the aniline can be reacted with oxaloyl chloride in a stepwise fashion, and the remaining acid chloride can be reacted with the aromatic ring via Friedel-Crafts acylation conditions to form the cyclic structure. From there, the amine can further react with an appropriately functionalized benzyl halide to form the benzylamine moiety.

Synthesis of Compounds of Formula M

The compounds of Formula M can be formed from appropriately functionalized 5-membered ring heteroaryls. The amine moiety can be formed by initial nitration, which tends to form nitro groups in the 2-position, and subsequent reduction to an amine group (which may be postponed until the other moieties are present). Halogenation occurring after the nitration step can place a halo group at the 3-position, which can then be nucleophilically displaced by a cyanide ion to form the nitrile, or converted to an organolithium reagent and reacted, for example, with cyanogen bromide to form the nitrile moiety. The side chain (alkylaryl, ether, and the like) can be incorporated using standard chemistry, such as nucleophilic substitution using an organolithium reagent.

Synthesis of Compounds of Formula N

The compounds of Formula N include urea, thiourea, and other similar moieties. At least one of these moieties includes an O, S, or N linked to an aryl ring, so the compounds can be synthesized from an appropriately functionalized phenyl isocyanate, thioisocyanate, and the like by nucleophilic reaction with an appropriately functionalized amine, thiol, or hydroxy-containing material (i.e., $R_1$—XH).

Synthesis of Compounds of Formula O

The compounds of Formula O include a naphthalene ring, and a cyclic ring structure including an imide moiety. The compounds can be prepared from naphthalene dicarboxylic acids and a suitably functionalized aniline in much the same way as phthalimide is formed (i.e., ring cyclization as the amine reacts with the acids, or activated forms thereof). Alternatively, the acids or activated forms thereof, such as anhydrides, acid chlorides, and the like, can be reacted with ammonia, which is then reacted with an aryl-diazonium salt to form the aniline.

Synthesis of Compounds of Formula P The compounds of Formula P include a naphthalene ring, and a) a cyclic ring structure including two ring nitrogens originating at positions 1 and 8 on the naphthalene ring, b) a cyclic ring structure including one ring nitrogen originating at position 1 or 8 on the naphthalene ring, and a methylamine moiety at the other of these positions, or c) two amines, at positions 1 and 8 on the naphthalene ring. Naphthalene 1,8 diamine is a commercially available compound whose synthesis need not be discussed herein. Alkylamines can be formed by reacting an amine (or ammonia) with a —$CH_2Br$ moiety at the 1 or 8 position, or with another naphthyl halide at this position. Rings with adjacent ring nitrogens can be formed, for example, by stepwise reaction of suitably functionalized hydrazines with diazonium salts (to form a linkage directly on an aromatic ring) or a —$CH_2Br$ moiety on the naphthalene ring (or other suitable leaving group other than bromide on such moiety).

Synthesis of Compounds of Formula Q

The compounds of Formula Q include an amide, ester, thioester, or similar linkage, where to the left and right of the carbonyl/thiocarbonyl moiety lie an aryl or arylalkyl moiety. These compounds can be prepared from suitably functionalized benzoic acid or phenyl-alkanoic acid by forming an acid halide or anhydride (or versions thereof where the carbonyl is replaced by a C(=S) or C(=$NR_1$) moiety), and reacting with a suitably functionalized phenol, thiophenol, aniline, or aryl-substituted hydroxyalkane, thioalkane, or amine.

Synthesis of Compounds of Formula R

The compounds of Formula R are functionalized cyclic ureas. They can be formed from suitably functionalized diamines (with amine moieties on adjacent carbon atoms) by reaction with phosgene, diphosgene, triphosgene, and the like. The carbonyl side chain can be formed, for example, by converting a carboxylic acid to an acid halide, and reacting the acid halide with a suitable Grignard or organolithium reagent.

Synthesis of Compounds of Formula S

The compounds of Formula S are functionalized cyclic ureas. They can be formed from suitably functionalized rings of the formula:

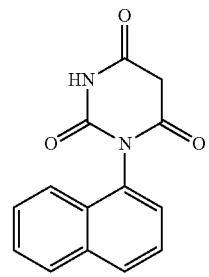 [SMILES: O=C1CC(=O)N(c2cccc3ccccc23)C(=O)N1]

by deprotonation with a strong base, followed by reaction with a compound of the formula:

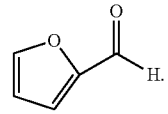

The resulting alcohol can then be dehydrated to form the compounds of Formula S.

Synthesis of Compounds of Formula T

The compounds of Formula T can be formed by reacting a compound of the formula:

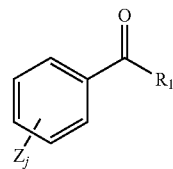

with a suitable hydrazine of the formula:

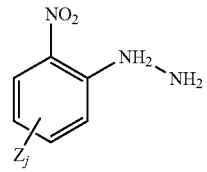

Additional synthetic details are provided below:

Synthesis of Compounds of Formula V

The compounds of Formula V can be prepared by reacting a compound of formula:

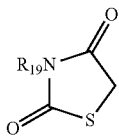

with a suitable strong base, and reacting the resulting carbanion with a suitably functionalized benzaldehyde. The resulting benzyl alcohol can be dehydrated to form the compounds of Formula V.

Preparing the 4,5-Bis(Diamino)-1-Naphthaldehyde Framework 1,8-diamino naphthalene is commercially available, and is used as a starting material for other commercially available analogs, such as proton sponge (1,8-bis-dimethylamino naphthalene).

To prepare the simplest analog, where R1-R4 are H, one can react 1,8-diamino naphthalene with carbon monoxide in a Friedel Craft reaction can produce the formyl group at a para-position to one of the amino groups. See, for example, "Aldehyde Syntheses" G. A. Olah, et al., Friedel-Crafts and Related Reactions, Wiley-Interscience, vol. III, Chapter XXXVIII, pp. 1153-1256, 1964. "Superacid-Catalyzed Formylation of Aromatics with Carbon Monoxide," G. A. Olah et al., J. Org. Chem., vol. 50, pp. 1483-1486, 1985. Note that the numbering on the naphthalene ring changes as the formyl substituent is added (i.e., formyl becomes the 1-position, and the amino groups are numbered accordingly, going from 1,8-diamino to 4,5-diamino). This chemistry is shown below in Scheme 1.

Scheme 1

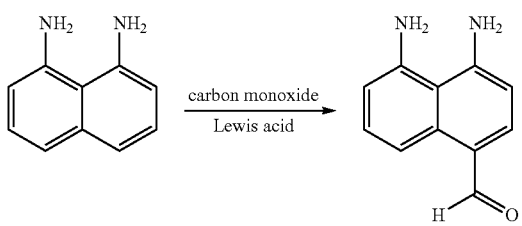

N-Alkylation/Arylation

Either before or after the Friedel Crafts reaction to put the formyl substituent on the naphthalene ring, one can react one or both of the amino groups (—$NH_2$) with an alkylating reagent to alkylate one or both of the amine groups, depending on stoichiometry.

For example, proton sponge (the bis-dimethylamino analogue of 1,8-diaminonaphthalene) is prepared by reacting 1,8-diaminonaphthalene with dimethyl sulfate.

Suitably functionalized aryl groups (i.e., aryl rings with any desired substitution) can be prepared that include a diazonium moiety at the position in which it is desired to attach the aryl group to the amine moiety(ies) on the 1,8-diaminonaphthalene. The amine moiety(ies) can then displaced the diazonium moiety to provide aryl amines.

Protecting groups can be used when it is desirable to alkylate/arylate one amino group in preference to the other. For example, one can selectively protect either the 1-amine or the 8-amine in the 1,8-diaminonaphthalene starting material, for example, using a t-boc or other protecting groups, such as those described in Greene and Wuts, Protective Groups in Organic Synthesis, 3rd Edition, June 1999, John Wiley & Sons Inc., the contents of which are hereby incorporated by reference. Then, following the alkylation/arylation reaction(s), the protective groups can be removed. The aldehyde group can be protected, for example, as an acetal group, which can be deprotected at a later time by simply reacting the acetal with water in the presence of an acid catalyst.

Substitution at Positions 2, 3, 6, 7, and 8

Where it is desirable to provide substitution at positions 2, 3, 6, 7, and 8 on the naphthalene ring, electrophilic aromatic substitution can be used to provide other desired functionality. For example, alkyl, aryl, heteroaryl, alkaryl, arylalkyl, alkenyl, alkynyl, and acyl groups can be added using Friedel-Crafts alkylation/arylation/acylation reactions. Other electrophilic aromatic substitution reactions can be used, for example, to provide halogens, such as by forming chloronium or bromonium ions in situ and reacting them with the aromatic ring, or by forming sulfonium or nitronium ions to provide sulfonyl or nitro groups.

Friedel Crafts alkylation is conducted using an appropriate halo-alkyl moiety, and a Lewis acid. The alkyl moiety forms a carbocation, and electrons from the aryl ring form a bond with the carbocation, placing a positive charge on the aryl ring. The aryl ring then loses a proton. Alkyl and alkaryl moieties (such as benzyl moieties) can be added in this fashion.

Friedel Crafts acylation is similar, but uses an acid halide, such as an acid chloride, to place a ketone moiety on the ring. The acid halide can be an alkyl acid, such as acetic acid, propionic acid, butyric acid, and the like, or can be an aromatic acid, such as benzoic acid, p-toluic acid, and the like.

Friedel Crafts arylation (also known as the Scholl reaction) is a coupling reaction with two aryl rings, catalyzed by a Lewis acid. The proton lost during the coupling reaction serves as an additional catalyst. Typical Reagents are iron(III) chloride in dichloromethane, copper(II) chloride, PIFA and boron trifluoride etherate in dichloromethane, Molybdenum (V) chloride and lead tetraacetate with $BF_3$ in acetonitrile.

Substitution typically occurs at a position ortho or para to the amine groups. So, positions 3, 6, and 8 are typically functionalized using this chemistry. Substitution of the naphthalene ring at a meta position to the amine groups (i.e., positions 2 and 7) can be performed by oxidizing the amine group(s) to nitro groups, which leads to meta substitution. The nitro groups can then be reduced back to the amine groups.

Formation of Heterocyclic Rings Incorporating the Amino Groups

Either or both of the amino groups in the 1,8-diamino naphthalene starting material, or in 4,5-bis(amino)-1-naphthaldehyde, can be cyclized using a di-halo compound. For example, a five membered ring can be formed using nucleophilic substitution. The amine is reacted with a 1,4-di-halobutane, such as 1,4-dibromobutane, and a six membered ring can be formed using a 1,5-dihalopentane, such as 1,5-dibromopentane. The reaction typically takes place in the presence of a tertiary amine, which reacts with the in situ-formed hydrogen halide, such as hydrogen bromide.

When it is desirable to incorporate an additional heteroatom into the cyclic group, one or more of the carbons in the dihaloalkane can be replaced with a heteroatom, such as O, S, or N (where the N can be substituted with an alkyl, aryl, alkaryl, aralkyl, or other such substituent).

Preparation of the Naphtho[2',3':4,5]imidazo[1,2-a]pyridine-6,11-dione Framework The compound 2,3-dichloro-1,4-naphthoquinone is commercially available, and is described, for example, in Honda, Nakanishi and Tabe, Bull. Chem Soc. Japan, 56(8):2338-2340 (1983), the contents of which are hereby incorporated by reference.

The carbonyl moieties on this compound can be protected, for example, as an ethylene ketal, and then reacted with 2-hydroxypyridine, the tautomer of which has the formula:

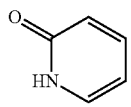

to provide an intermediate in which the pyridine nitrogen reacts with one of the ring halogens. Nucleophilic displacement of the halogen with ammonia (or an amine, if an N-alkyl, N-aryl, or other such derivative is desired) affords an amine group, which cyclizes with the carbonyl moiety in the pyridine to form an imine linkage in a ring-closure step. Deprotection of the ketone moieties, and catalytic dehydrogenation, afford the final product. This chemistry is shown below in Scheme 2.

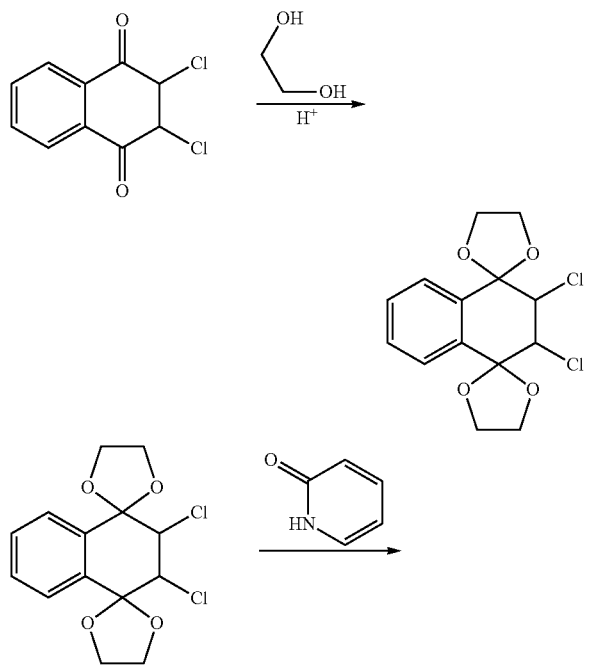

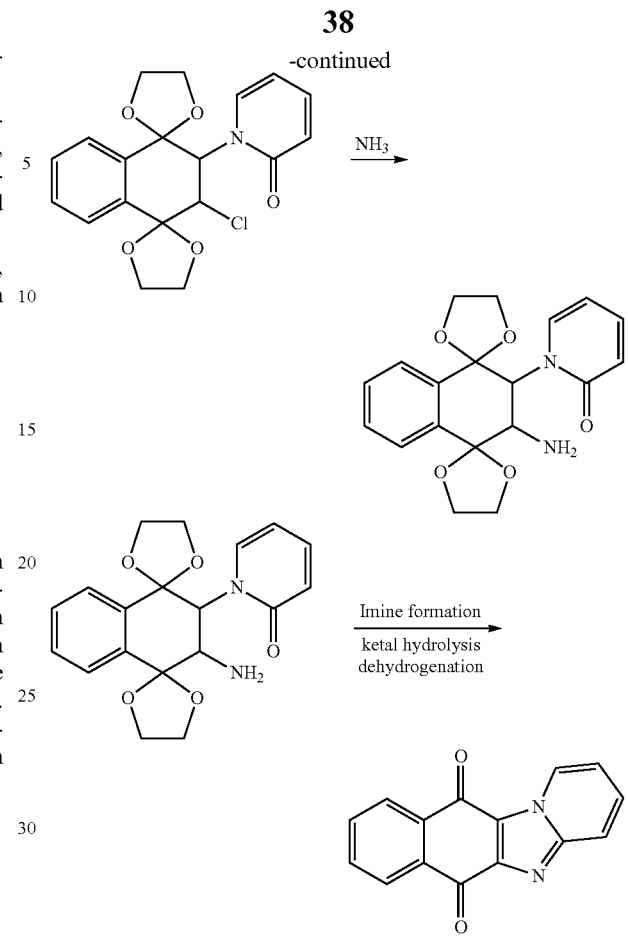

As described above with respect to formation of the 4,5-bis(diamino)-1-naphthaldehyde compounds, substitution on the aromatic ring (substituents R4-R7) can be performed using Friedel Crafts alkylation, acylation, or arylation, or other known electrophilic aromatic substitution. Substitution of the pyridine ring (i.e., R15-17) can be performed using well-known substitution reactions for producing pyridine analogs. These substitution reactions include electrophilic aromatic substitution, and nucleophilic aromatic substitution reactions.

Electrophilic Aromatic Substitution on Pyridine

Electrophiles react preferentially with the lone pair of the nitrogen to generate the pyridinium ion which, being positively charged, is unreactive towards electrophilic substitution. Neutral pyridine, which can react with electrophiles, is present only in a very low equilibrium concentration, so the rate of electrophilic aromatic substitution reactions is slow relative to aromatic rings.

The ring nitrogen polarizes the p-electron system, resulting in decreased electron density on the carbons, and as a result, electrophilic substitution typically forms 3-substituted products (the 3-position is the least disfavored position). This is analogous to how a nitro-substituent directs electrophilic substitution of benzene to the meta position.

Nucleophilic Aromatic Substitution on Pyridine

Pyridines are susceptible to nucleophilic attack at C-2 and C-4. By analogy with nitrobenzene, 2- or 4-halopyridines will undergo preferential substitution of the halide, compared to 3-halopyridines. Strongly basic nucleophiles, such as $NH_2^-$, and alkyllithium and aryllithium or comparable Grignard reagents, will add at C-2 to form the 2-substituted pyridine, even without a leaving group. Where the nucleophile is $NH_2^-$, the reaction is known as the Chichibabin reaction.

Enantiomeric Purification

As used herein, the term "enantiomerically pure" refers to a nucleotide composition that comprises at least approximately 95%, and, preferably, approximately 97%, 98%, 99% or 100% of a single enantiomer of that nucleotide.

As used herein, the term "substantially free of" or "substantially in the absence of" refers to a nucleotide composition that includes at least 85 to 90% by weight, preferably 95% to 98% by weight, and, even more preferably, 99% to 100% by weight, of the designated enantiomer of that nucleotide. In a preferred embodiment, the compounds described herein are substantially free of enantiomers.

Similarly, the term "isolated" refers to a nucleotide composition that includes at least 85 to 90% by weight, preferably 95% to 98% by weight, and, even more preferably, 99% to 100% by weight, of the nucleotide, the remainder comprising other chemical species or enantiomers.

The compounds described herein may have asymmetric centers and occur as racemates, racemic mixtures, individual diastereomers or enantiomers, with all isomeric forms being included in the present invention. Compounds of the present invention having a chiral center can exist in and be isolated in optically active and racemic forms. Some compounds can exhibit polymorphism. The present invention encompasses racemic, optically-active, polymorphic, or stereoisomeric forms, or mixtures thereof, of a compound of the invention, which possess the useful properties described herein. The optically active forms can be prepared by, for example, resolution of the racemic form by recrystallization techniques, by synthesis from optically-active starting materials, by chiral synthesis, or by chromatographic separation using a chiral stationary phase or by enzymatic resolution. One can either purify the respective nucleoside, then derivatize the nucleoside to form the compounds described herein, or purify the nucleotides themselves.

Optically active forms of the compounds can be prepared using any method known in the art, including but not limited to by resolution of the racemic form by recrystallization techniques, by synthesis from optically-active starting materials, by chiral synthesis, or by chromatographic separation using a chiral stationary phase.

Examples of methods to obtain optically active materials include at least the following.

i) physical separation of crystals: a technique whereby macroscopic crystals of the individual enantiomers are manually separated. This technique can be used if crystals of the separate enantiomers exist, e., the material is a conglomerate, and the crystals are visually distinct;

ii) simultaneous crystallization: a technique whereby the individual enantiomers are separately crystallized from a solution of the racemate, possible only if the latter is a conglomerate in the solid state;

iii) enzymatic resolutions: a technique whereby partial or complete separation of a racemate by virtue of differing rates of reaction for the enantiomers with an enzyme;

iv) enzymatic asymmetric synthesis: a synthetic technique whereby at least one step of the synthesis uses an enzymatic reaction to obtain an enantiomerically pure or enriched synthetic precursor of the desired enantiomer;

v) chemical asymmetric synthesis: a synthetic technique whereby the desired enantiomer is synthesized from an achiral precursor under conditions that produce asymmetry (i.e., chirality) in the product, which can be achieved using chiral catalysts or chiral auxiliaries;

vi) diastereomer separations: a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations: a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions: this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors: a synthetic technique whereby the desired enantiomer is obtained from non-chiral starting materials and where the stereochemical integrity is not or is only minimally compromised over the course of the synthesis;

x) chiral liquid chromatography: a technique whereby the enantiomers of a racemate are separated in a liquid mobile phase by virtue of their differing interactions with a stationary phase (including but not limited to via chiral HPLC). The stationary phase can be made of chiral material or the mobile phase can contain an additional chiral material to provoke the differing interactions;

xi) chiral gas chromatography: a technique whereby the racemate is volatilized and enantiomers are separated by virtue of their differing interactions in the gaseous mobile phase with a column containing a fixed non-racemic chiral adsorbent phase;

xii) extraction with chiral solvents: a technique whereby the enantiomers are separated by virtue of preferential dissolution of one enantiomer into a particular chiral solvent;

xiii) transport across chiral membranes: a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

Chiral chromatography, including but not limited to simulated moving bed chromatography, is used in one embodiment. A wide variety of chiral stationary phases are commercially available.

III. Methods of Treatment

The compounds described herein are capable of inhibiting viral propagation. The retroviral propagation can be inhibited by inhibiting retroviral reverse transcription, viral recruitment of the retroviral primer used in translation, human $tRNA^{Lys3}$, inhibiting the final packaging and assembly of new virions, and/or inhibiting the binding of a host cell tRNA to a target nucleic acid molecule.

Accordingly, these compounds can be used in methods to treat patients suffering from retroviral infections. That is, a retroviral viral infection can be treated or prevented by administering one or more inhibitors of retroviral propagation, for example, inhibitors of retroviral reverse transcription, binding to host cell tRNA and a target nucleic acid molecule, recruitment of the retroviral primer, human tRNA$^{Lys3}$, viral RNA translation into viral proteins, and final viral packaging and assembly of virions. Treatment of viral disease has not been heretofore accomplished by using such inhibitors.

The compounds can be used to treat or prevent viral infections, including infections by retroviruses, and/or to inhibit viral replication, propagation, reverse transcription, mRNA translation, and/or final viral packaging and assembly. Retroviruses for which inhibitors can be identified by the methods disclosed herein include any viruses having RNA as their primary genetic material and use reverse transcription to produce DNA. Such viruses include, but are not limited to, Feline Immunodeficiency Virus (FIV), Simian Immunodeficiency Virus (SIV), Avian Leucosis Virus, Feline Leukemia Virus, Walleye Dermal Sarcoma Virus, Human T-Lymphotropic Virus, and Human Immunodeficiency Viruses (HIV). In a preferred aspect, the retrovirus is HIV. HIV can be any strain, form, subtype or variation in the HIV family. HIV viruses include, but are not limited to, HIV-I, HIV-II, HIV-III (also known as HTLV-II, LAV-I, LAV-2), and the like.

The compounds can also be used as adjunct therapy in combination with existing therapies in the management of the aforementioned types of viral infections. In such situations, it is preferably to administer the active ingredients to a patient in a manner that optimizes effects upon viruses, including mutated, multi-drug resistant viruses, while minimizing effects upon normal cell types. While this is primarily accomplished by virtue of the behavior of the compounds themselves, this can also be accomplished by targeted drug delivery and/or by adjusting the dosage such that a desired effect is obtained without meeting the threshold dosage required to achieve significant side effects.

Retroviruses whose infection can be treated or prevented using the inhibitors described herein include any viruses having RNA as their primary genetic material and use reverse transcription to produce DNA. Such viruses include, but are not limited to, Feline Immunodeficiency Virus (FIV), Simian Immunodeficiency Virus (SIV), Avian Leucosis Virus, Feline Leukemia Virus, Walleye Dermal Sarcoma Virus, Human T-Lymphotropic Virus, and Human Immunodeficiency Viruses (HIV). In a preferred aspect, the retrovirus is HIV. HIV can be any strain, form, subtype or variation in the HIV family. HIV viruses include, but are not limited to, HIV-I, HIV-II, HIV-III (also known as HTLV-II, LAV-I, LAV-2), mutated versions thereof, and the like.

Inhibitors of HIV are also active against the hepatitis B virus (HBV), and can be used in methods of treating and/or preventing HBV infection, and pharmaceutical compositions intended for this use.

IV. Pharmaceutical Compositions

The inhibitory compounds as described herein can be incorporated into pharmaceutical compositions and used to treat or prevent a viral infection, such as a retroviral infection. The pharmaceutical compositions described herein include the inhibitory compounds as described herein, and a pharmaceutically acceptable carrier and/or excipient.

The manner in which the compounds are administered can vary. The compositions are preferably administered orally (e.g., in liquid form within a solvent such as an aqueous or non-aqueous liquid, or within a solid carrier). Preferred compositions for oral administration include pills, tablets, capsules, caplets, syrups, and solutions, including hard gelatin capsules and time-release capsules. Compositions may be formulated in unit dose form, or in multiple or subunit doses. Preferred compositions are in liquid or semisolid form. Compositions including a liquid pharmaceutically inert carrier such as water or other pharmaceutically compatible liquids or semisolids may be used. The use of such liquids and semisolids is well known to those of skill in the art.

The compositions can also be administered via injection, i.e., intraveneously, intramuscularly, subcutaneously, intraperitoneally, intraarterially, intrathecally; and intracerebroventricularly. Intravenous administration is a preferred method of injection. Suitable carriers for injection are well known to those of skill in the art, and include 5% dextrose solutions, saline, and phosphate buffered saline. The compounds can also be administered as an infusion or injection (e.g., as a suspension or as an emulsion in a pharmaceutically acceptable liquid or mixture of liquids).

The formulations may also be administered using other means, for example, rectal administration. Formulations useful for rectal administration, such as suppositories, are well known to those of skill in the art. The compounds can also be administered by inhalation (e.g., in the form of an aerosol either nasally or using delivery articles of the type set forth in U.S. Pat. No. 4,922,901 to Brooks et al., the disclosure of which is incorporated herein in its entirety); topically (e.g., in lotion form); or transdermally (e.g., using a transdermal patch, using technology that is commercially available from Novartis and Alza Corporation). Although it is possible to administer the compounds in the form of a bulk active chemical, it is preferred to present each compound in the form of a pharmaceutical composition or formulation for efficient and effective administration.

Exemplary methods for administering such compounds will be apparent to the skilled artisan. The usefulness of these formulations may depend on the particular composition used and the particular subject receiving the treatment. These formulations may contain a liquid carrier that may be oily, aqueous, emulsified or contain certain solvents suitable to the mode of administration.

The compositions can be administered intermittently or at a gradual, continuous, constant or controlled rate to a warm-blooded animal (e.g., a mammal such as a mouse, rat, cat, rabbit, dog, pig, cow, or monkey), but advantageously are administered to a human being. In addition, the time of day and the number of times per day that the pharmaceutical formulation is administered can vary.

Preferably, the compositions are administered such that active ingredients interact with regions where viral infections are located. The compounds described herein are very potent at treating these viral infections.

In certain circumstances, the compounds described herein can be employed as part of a pharmaceutical composition with other compounds intended to prevent or treat a particular viral infection, i.e., combination therapy. In addition to effective amounts of the compounds described herein, the pharmaceutical compositions can also include various other components as additives or adjuncts.

Combination or Alternation Therapy

In one embodiment, the compounds of the invention can be employed together with at least one other antiviral agent, chosen from entry inhibitors, reverse transcriptase inhibitors, protease inhibitors, and immune-based therapeutic agents.

For example, when used to treat or prevent HIV infection, the active compound or its prodrug or pharmaceutically acceptable salt can be administered in combination or alternation with another anti-HIV agent. In general, in combination therapy, effective dosages of two or more agents are administered together, whereas during alternation therapy, an effective dosage of each agent is administered serially. The dosage will depend on absorption, inactivation and excretion rates of the drug, as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

Combination therapy may be administered as (a) a single pharmaceutical composition which comprises an inhibitory compound as described herein, at least one additional pharmaceutical agent described herein, and a pharmaceutically acceptable excipient, diluent, or carrier; or (b) two separate pharmaceutical compositions comprising (i) a first composition comprising an inhibitory compound as described herein and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions can be administered simultaneously or sequentially and in any order.

In use in treating or preventing viral disease, the inhibitory compound(s) can be administered together with at least one other antiviral agent as part of a unitary pharmaceutical composition. Alternatively, it can be administered apart from the other antiviral agents. In this embodiment, the inhibitory compound and the at least one other antiviral agent are administered substantially simultaneously, i.e. the compounds are administered at the same time or one after the other, so long as the compounds reach therapeutic levels for a period of time in the blood.

Combination therapy involves administering the inhibitory compound, as described herein, or a pharmaceutically acceptable salt or prodrug of the inhibitory compound, in combination with at least one anti-viral agent, ideally one which functions by a different mechanism than the inhibitors of viral propagation described herein.

Representative Antiviral Agents

Some antiviral agents which can be used for combination therapy include agents that interfere with the ability of a virus to infiltrate a target cell. The virus must go through a sequence of steps to do this, beginning with binding to a specific "receptor" molecule on the surface of the host cell and ending with the virus "uncoating" inside the cell and releasing its contents. Viruses that have a lipid envelope must also fuse their envelope with the target cell, or with a vesicle that transports them into the cell, before they can uncoat.

There are two types of active agents which inhibit this stage of viral replication. One type includes agents which mimic the virus-associated protein (VAP) and bind to the cellular receptors, including VAP anti-idiotypic antibodies, natural ligands of the receptor and anti-receptor antibodies, receptor anti-idiotypic antibodies, extraneous receptor and synthetic receptor mimics. The other type includes agents which inhibit viral entry, for example, when the virus attaches to and enters the host cell. For example, a number of "entry-inhibiting" or "entry-blocking" drugs are being developed to fight HIV, which targets the immune system white blood cells known as "helper T cells", and identifies these target cells through T-cell surface receptors designated "CRX4" and "CCR5". Thus, CRX4 and CCR5 receptor inhibitors such as amantadine and rimantadine, can be used to inhibit viral infection, such as HIV, influenza, and hepatitis B and C viral infections. Another entry-blocker is pleconaril, which works against rhinoviruses, which cause the common cold, by blocking a pocket on the surface of the virus that controls the uncoating process.

Further antiviral agents that can be used in combination with the inhibitory compounds described herein include agents which interfere with viral processes that synthesize virus components after a virus invades a cell. Representative agents include nucleotide and nucleoside analogues that look like the building blocks of RNA or DNA, but deactivate the enzymes that synthesize the RNA or DNA once the analogue is incorporated. Acyclovir is a nucleoside analogue, and is effective against herpes virus infections. Zidovudine (AZT), 3TC, FTC, and other nucleoside reverse transcriptase inhibitors (NRTI), as well as non-nucleoside reverse transcriptase inhibitors (NNRTI), can also be used. Integrase inhibitors can also be used.

Once a virus genome becomes operational in a host cell, it then generates messenger RNA (mRNA) molecules that direct the synthesis of viral proteins. Production of mRNA is initiated by proteins known as transcription factors, and certain active agents block attachment of transcription factors to viral DNA.

Other active agents include antisense oligonucleotides and ribozymes (enzymes which cut apart viral RNA or DNA at selected sites).

Some viruses, such as HIV, include protease enzymes, which cut viral protein chains apart so they can be assembled into their final configuration. Protease inhibitors are another type of antiviral agent that can be used in combination with the inhibitory compounds described herein.

The final stage in the life cycle of a virus is the release of completed viruses from the host cell. Some active agents, such as zanamivir (Relenza) and oseltamivir (Tamiflu) treat influenza by preventing the release of viral particles by blocking a molecule named neuraminidase that is found on the surface of flu viruses.

Still other active agents function by stimulating the patient's immune system. Interferons, including pegylated interferons, are representative compounds of this class. Interferon alpha is used, for example, to treat hepatitis B and C. Various antibodies, including monoclonal antibodies, can also be used to target viruses.

Any of the above-mentioned compounds can be used in combination therapy with the inhibitors described herein.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder.

When treating viral infections, an effective amount of the inhibitory compound is an amount sufficient to suppress the growth and proliferation of the virus. Viral infections can be prevented, either initially, or from re-occurring, by administering the compounds described herein in a prophylactic manner. Preferably, the effective amount is sufficient to obtain the desired result, but insufficient to cause appreciable side effects.

The effective dose can vary, depending upon factors such as the condition of the patient, the severity of the viral infection, and the manner in which the pharmaceutical composition is administered. The effective dose of compounds will of course differ from patient to patient, but in general includes amounts starting where desired therapeutic effects occur but below the amount where significant side effects are observed.

The compounds, when employed in effective amounts in accordance with the method described herein, are effective at inhibiting the proliferation of certain viruses, but do not significantly effect normal cells.

For human patients, the effective dose of typical compounds generally requires administering the compound in an amount of at least about 1, often at least about 10, and frequently at least about 25 µg/24 hr/patient. The effective dose generally does not exceed about 500, often does not exceed about 400, and frequently does not exceed about 300 µg/24 hr/patient. In addition, administration of the effective dose is such that the concentration of the compound within the plasma of the patient normally does not exceed 500 ng/mL and frequently does not exceed 100 ng/mL.

V. Methods for Identifying an Inhibitor of Retroviral Propogation

The compounds described herein can be evaluated for their ability to inhibit viral propagation, for example, retroviral propagation, using the methods described herein. The retroviral propagation can be inhibited, for example, by a) inhibiting retroviral reverse transcription,
b) inhibiting the binding of a host cell tRNA and a target nucleic acid molecule,
c) inhibiting the viruses recruitment of the retroviral primer, human tRNA$^{Lys3}$,
d) inhibiting HIV translation of viral RNA to precursor proteins, and/or
e) inhibiting HIV's final packaging and assembly.

These individual methods for identifying inhibitors of retroviral propagation are discussed below.

Identifying Inhibitors of Retroviral Reverse Transcription

In one aspect, putative inhibitors of retroviral reverse transcription can be identified. In another aspect, putative inhibitors of tRNA's ability to bind to a target nucleic acid molecule can be identified. The identification can be done in in a high through-put manner. Transfer RNA (tRNA) is involved in reverse transcription through the recognition of a corresponding site on the retroviral genome priming reverse transcription. Identifying inhibitors of reverse transcription may lead to the identification of therapeutic compounds for use in treating retroviral infection in a host cell.

The screening methods involve forming a mixture having a tRNA anticodon stem-loop (ASL) fragment, a target nucleic acid molecule that is capable of binding to the tRNA fragment, and a test compound. In one aspect, the target nucleic acid molecule corresponds to a fragment of the retroviral genome involved in reverse transcription. The resulting mixture is incubated under conditions that allow binding of the tRNA fragment and the target nucleic acid in the absence of the test compound. The method further involves detecting whether the test compound inhibits the binding of the tRNA fragment to the target nucleic acid, where the absence of binding of the tRNA ASL fragment and the target nucleic acid molecule is indicative of the test compound being an inhibitor of retroviral reverse transcription. In one aspect, the detection involves the use of labels to detect the inhibition of binding of the tRNA fragment to the target nucleic acid molecule.

Methods for Identifying Inhibitors of Binding of a Host Cell tRNA to a Target Nucleic Acid Molecule In another aspect, the ability of a putative inhibitor to bind a tRNA to a target nucleic acid molecule can be assayed. The assay involves forming a mixture containing a host cell tRNA ASL fragment, a target nucleic acid molecule that is capable of binding to the tRNA fragment, and a test compound. The resulting mixture is incubated under conditions that allow binding of the tRNA fragment and the target nucleic acid in the absence of the test compound. The method further involves detecting whether the test compound inhibits the binding of the tRNA fragment to the target nucleic acid, where binding of the tRNA ASL fragment and the target nucleic acid molecule is indicative of the test compound being an inhibitor of binding of a tRNA to a target nucleic acid molecule. In one aspect, the detection involves the use of labels to detect the inhibition of binding of the tRNA fragment to the target nucleic acid molecule.

Methods for Identifying Inhibitors of HIV Reverse Transcription (RT) Complex Formation In another aspect, the ability of a compound to function as an inhibitor of HIV reverse transcriptase (RT) complex formation can be assayed. The assay involves forming a mixture containing a tRNA ASL fragment, a target nucleic acid molecule capable of binding to the tRNA fragment, and a test compound. The resulting mixture is incubated under conditions that allow binding of the tRNA fragment and the target nucleic acid in the absence of the test compound. The method further involves detecting whether the test compound inhibits the binding of the tRNA fragment to the target nucleic acid. In one aspect, the detection involves the use of labels to detect the inhibition of binding of the tRNA fragment to the target nucleic acid molecule, where the inhibition indicates that the test compound is capable of inhibiting the formation of the RT complex.

In another aspect, the assay may involve detecting the binding of the putative inhibitor to either the tRNA fragment, the target nucleic acid, or both the tRNA fragment and the target nucleic acid. In one aspect, the binding of the putative inhibitor is indicative of the test compound being an inhibitor of retroviral propagation, retroviral infection, reverse transcription, or tRNA binding.

Methods for Identifying Inhibitors of Viral Recruitment of Human tRNA$^{Lys3}$.

In yet another aspect, the ability of a putative inhibitor to inhibit HIV's recruitment of the retroviral primer, human tRNA$^{Lys3}$ can be assayed. The assay involves forming a mixture comprising a linear sequence of a tRNA anticodon stem loop fragment that is not capable of forming a stem-loop, a target nucleic acid molecule capable of binding to the tRNA anticodon stem loop fragment, and a test compound, wherein the target nucleic acid molecule corresponds to a portion of a retroviral genome involved in recruitment of retroviral primer recruitment. The mixture is incubated under conditions that allow binding of the tRNA anticodon stem loop fragment and the target nucleic acid molecule in the absence of the test compound. One can then detect whether or not the test compound inhibits the binding of the tRNA anticodon stem loop fragment and the target nucleic acid molecule. The absence of binding of the tRNA ASL fragment and the target nucleic acid molecule is indicative of the test compound being an inhibitor retroviral primer recruitment.

Methods for Identifying Inhibitors of Viral RNA Translation

In still another aspect, a ability of a putative inhibitor of viral RNA translation to viral precursor proteins can be assayed. The assay involves forming a mixture comprising a linear sequence of a tRNA anticodon stem loop fragment that is not capable of forming a stem-loop, a target nucleic acid molecule capable of binding to the tRNA anticodon stem loop fragment, and a test compound; incubating the mixture under conditions that allow binding of the tRNA anticodon stem loop fragment and the target nucleic acid molecule in the absence of the test compound; and detecting whether or not the test compound inhibits the binding of the tRNA fragment and the target nucleic acid molecule where binding of the tRNA ASL fragment and the target nucleic acid molecule is indicative of the test compound being an inhibitor of tRNA recruitment during viral RNA translation to viral precursor proteins.

The inhibitors can inhibit the retroviral infection by inhibiting any step of a virus lifecycle, including, but not limited to, reverse transcription, viral assembly, RT complex formation, recruitment of the retroviral primer, human tRNA$^{Lys3}$, translation of viral RNA to precursor proteins, and the final packaging and assembly. Moreover, the inhibitors may inhibit retroviral infection, delay the infection, or slow the progression of the infection.

VI. tRNA Fragments Useful in the Methods Described Herein

The tRNA fragments (or "tool tRNA fragments") for use in the screening methods described herein can be a fragment from any tRNA. Specific tRNA fragments described in the formulas below are another aspect of the invention, and these fragments can be included in the kits described herein.

The tRNA fragments (or "tool tRNA fragments") for use in the methods of the present disclosure can be a fragment from any tRNA. The tRNA fragment may be obtained or derived from or corresponds to a tRNA$^{Ala}$, tRNA$^{Arg}$, tRNA$^{Asn}$, tRNA$^{Asp}$, tRNA$^{Cys}$, tRNA$^{Gln}$, tRNA$^{Glu}$, tRNA$^{Gly}$, tRNA$^{His}$, tRNA$^{Ile}$, tRNA$^{Leu}$, tRNA$^{Lys}$, tRNA$^{Met}$, tRNA$^{Phe}$, tRNA$^{Pro}$, tRNA$^{Ser}$, tRNA$^{Thr}$, tRNA$^{Trp}$, tRNA$^{Tyr}$, and tRNA$^{Val}$. In one aspect, the tRNA fragment corresponds to tRNA$^{Lys}$. In another aspect, the tRNA fragment is derived from or corresponds to the tRNA$^{Lys}$ anticodon stem loop (ASL). In another aspect, the tRNA fragment corresponds to a fragment of nucleotides 32-43 of the human tRNA$^{Lys}$. The position numbers used herein refer to the nucleotide position numbering of the conventional tRNA numbering as disclosed in Sprinzl, et al. Nucl. Acids. Res., 26, 148-153 (1998). In one aspect, the tRNA fragment is a fragment from a host cell tRNA, such as a mammalian host cell, including, but not limited to, human, feline, and simian host cells.

The tRNA fragments may incorporate one or more modified nucleosides. In one aspect, the tRNA fragment incorporates one, two, three, or more modified nucleosides into the nucleic acid sequence. In another aspect, the tRNA fragments incorporate three modified nucleosides into the tRNA fragment nucleic acid molecules. Modified nucleosides that can be incorporated into the tRNA fragments include any modified nucleotide, including, but not limited to unknown modified adenosine (?A), 1-methyladenosine (m1A), 2-methyladenosine (m2A), N$^6$-isopentenyladenosine (i6A), 2-methylthio-N$^6$-isopentenyladenosine (ms2i6A), N$^6$-methyladenosine (m6A), N$^6$-threonylcarbamoyladenosine (t6A), N$^6$-methyl-N$^6$ threonylcarbomoyladenosine (m6t6A), 2-methylthio-N$^6$-threonylcarbamoyladenosine (ms2t6A), 2'-O-methyladenosine I Inosine (Am), 1-methylinosine Ar(p) 2'-O-(5-phospho)ribosyladenosine (m1I), N$^6$-(cis-hydroxyisopentenyl)adenosine (io6A), Unknown modified cytidine (?C), 2-thiocytidine (s2C), 2'-O-methylcytidine (Cm), N$^4$-acetylcytidine (ac4C), 5-methylcytidine (m5C), 3-methylcytidine (m3C), lysidine (k2C), 5-formylcytidin (f5C), 2'-O-methyl-5-formylcytidin (f5Cm), unknown modified guanosine (?G), 2'-O-(5phospho) ribosylguanosine (Gr(p)), 1-methylguanosine (m1G), N$^2$-methylguanosine (m2G), 2'-O-methylguanosine (Gm), N$^2$N$^2$-dimethylguanosine (m22G), N$^2$,N$^2$,2'-O-trimethylguanosine (m22Gm), 7-methylguanosine (m7G), archaeosine (fa7d7G), queuosine (Q), mannosyl-queuosine (manQ), galactosyl-queuosine (galQ), wybutosine (yW), peroxywybutosine (02yW), unknown modified uridine (?U), 5-methylaminomethyluridine (mnm5U), 2-thiouridine (s2U), 2'-O-methyluridine (Um), 4-thiouridine (s4U), 5carbamoylmethyluridine (ncm5U), 5-methoxycarbonylmethyluridine (mcm5U), 5methylaminomethyl-2-thiouridine (mnm5s2U), 5-methoxycarbonylmethyl-2-thiouridine (mcm5s2U), uridine 5-oxyacetic acid (cmo5U), 5-methoxyuridine (mo5U), 5carboxymethylaminomethyluridine (cmnm5U), 5-carboxymethylaminomethyl-2-thiouridine (cmnm5s2U), 3-(3-amino-3-carboxypropyl) uridine (acp3U), 5-(carboxyhydroxymethyl)uridinemethyl ester (mchm5U), 5-carboxymethylaminomethyl-2'-O-methyluridine (cmnm5Um), 5-carbamoylmethyl-2'-O-methyluridine (ncm5Um), Dihydrouridine (D), pseudouridine (ψ), 1-methylpseudouridine (m1ψ), 2'-O-methylpseudouridine (ψm), ribosylthymine (m5U), 5-methyl-2-thiouridine (m5s2U), and 5,2'-O-dimethyluridine (m5Um).

In a preferred aspect, the fragment tRNA contains modified nucleic acids corresponding to positions 34, 37, and 39 in the anticodon stem loop of a tRNA. The position numbers used herein refer to the nucleotide position numbering of the conventional tRNA numbering as disclosed in Sprinzl, et al. Nucl. Acids. Res., 26, 148-153 (1998). In one aspect, the tRNA fragment comprises, or consists of, a molecule having the sequence 5'-GCUXUUAYZCUG, in which the X, Y, and Z refer to modified or unmodified nucleosides. In one aspect, the X, Y, and Z refer to modified nucleosides, such as mnm5s2U, mcm5s2U, ms2t6A, s2U, ψ, and t6A. In another aspect, the tRNA fragment has the nucleic acid sequence 5'-CU(mnm5s2U)UU(ms2t6A)A(ψ)CUGC. In another aspect, the tRNA fragment has the nucleic acid sequence 5'-GCU(mnm5s2U)UU(ms2t6A)A(ψ)CUG.

The tRNA fragment may correspond to any portion of the tRNA involved in propagation of the retrovirus through binding, directly or indirectly, to the retroviral genome. In a preferred aspect, the tRNA fragment corresponds to the anticodon stem loop (ASL) of the tRNA.

The tRNA fragment may correspond to any portion of the host cell's tRNA involved in nucleotide binding, such as involvement in the reverse transcription (RT) complex formation. For example, the tRNA may be involved in binding to a retroviral genome to initiate, prime, or facilitate reverse transcription of the retroviral genome. In one aspect, the fragment tRNA corresponds to a fragment of the anticodon stem loop of any tRNA. In one aspect, the fragment corresponds to a fragment from the anticodon stem loop of tRNA$^{-Lys}$. In another aspect, the tRNA fragment corresponds to a fragment from the anticodon stem loop of human tRNA$^{-Lys}$. In another aspect, the tRNA fragment corresponds to a fragment from nucleotides 32-43 of human tRNA$^{Lys3}$.

The tRNA fragment may also be any length of a fragment from a tRNA. In one aspect, the tRNA fragment comprises a fragment of between 9 to 15 continuous nucleotides of a tRNA, 10 to 14 continuous nucleotides of a tRNA, or between 11 to 13 continuous nucleotides of a tRNA. In another aspect, the fragment is a fragment of 8, 9, 10, 11, 12, 13, 14, 15, or 16 continuous nucleotides of a tRNA. In a further aspect, the fragment is a fragment of 12 continuous nucleotides of a tRNA.

The tRNA fragment may or may not be capable of forming a secondary structure. In a one aspect, the tRNA fragment is not capable of forming a stem loop structure with itself. In another aspect, the fragment is a linear fragment of a tRNA that is not capable of forming a stem loop structure with itself.

The tRNA fragment may also be linked to additional nucleic acids. For example, the tRNA fragment may be linked to one or more additional nucleic acids depending on the assay method. In one aspect, the tRNA fragment may be linked to nucleotides used to attach the fragment to a solid support surface. In another aspect, the fragment tRNA is linked to additional nucleic acid molecules at one or both terminal end of the tRNA fragment. In another aspect, the fragment tRNA is linked to additional nucleic acid molecules at both terminal ends. The additional nucleic acid sequences can be any length, preferably between 8 and 16 nucleotides, between 10 and 14 nucleotides, more preferably 12 nucleotides in length. In one aspect, the terminal sequences do not allow the tRNA fragment to form a secondary structure, such as a hairpin loop structure.

A target nucleic acid molecule may correspond to any nucleic acid molecule, such as a DNA or an RNA molecule that is involved in retroviral propagation or retroviral reverse transcription. In one aspect, the target nucleic acid molecule corresponds to any nucleic acid molecule that is capable of binding to the tRNA fragment and is involved in retroviral propagation or reverse transcription. In another aspect, the target nucleic acid molecule corresponds to a nucleic acid molecule involved in reverse transcription of a retroviral genome. In another aspect, the target nucleic acid molecule corresponds to ribonucleic acid from a retroviral genome. In another aspect, the target nucleic acid molecule corresponds to a nucleic acid molecule that is involved in priming retroviral reverse transcription.

The target nucleic acid molecule may be any length and may include the entire retroviral genome and fragments thereof. In one aspect, the target nucleic acid molecule includes any fragment of a retroviral genome involved in tRNA binding, and includes fragments of at least 5, 6, 7, 8, 9, 10, 11, 12, 13, 14, 15, 20, 25, 30, 35, 40, 45, 50 or more nucleotides. In another aspect, the target nucleic acid is about the same, or is the same length as the tool tRNA fragment.

In another aspect, the target nucleic acid molecule corresponds to a nucleic acid molecule from a Human Immunodeficiency Virus (HIV), such as HIV-1 or HIV-2. In another aspect, the target molecule corresponds to HIV-1. In another aspect, the target nucleic acid molecule corresponds to a nucleic acid molecule involved in priming HIV reverse transcription.

Such target nucleic acid molecules can be derived from or correspond to any portion of the HIV genome involved in reverse transcription through the binding or association with a host cell tRNA. In one aspect, the target nucleic acid molecule is derived from or corresponds to the 5' untranslated region of the HIV genome. In another aspect, the target nucleic acid molecule corresponds to a fragment including residues 157 to 169 of the 5' untranslated region of HIV-1. The target nucleic acid sequence may be complementary to the tRNA fragment. In a one aspect, the target nucleic acid molecule comprises the nucleic acid sequence 5'-GCGGUGUAAAAG.

Specific Isolated tRNA Fragments

In one aspect, the isolated tRNA fragment comprises the sequence 5'-GCUXUUAYZCUG, in which the X, Y, and Z refer to modified nucleosides.

Representative modified nucleosides include unknown modified adenosine (?A), 1-methyladenosine (m1A), 2-methyladenosine (m2A), $N^6$-isopentenyladenosine (i6A), 2-methylthio-$N^6$-isopentenyladenosine (ms2i6A), $N^6$-methyladenosine (m6A), $N^6$-threonylcarbamoyladenosine (t6A), $N^6$-methyl-$N^6$ threonylcarbomoyladenosine (m6t6A), 2-methylthio-$N^6$-threonylcarbamoyladenosine (ms2t6A), 2'-O-methyladenosine I Inosine (Am), 1-methylinosine Ar(p) 2'-O-(5-phospho)ribosyladenosine (m1I), $N^6$-(cis-hydroxyisopentenyl)adenosine (io6A), Unknown modified cytidine (?C), 2-thiocytidine (s2C), 2'-O-methylcytidine (Cm), $N^4$-acetylcytidine (ac4C), 5-methylcytidine (m5C), 3-methylcytidine (m3C), lysidine (k2C), 5-formylcytidin (f5C), 2'-O-methyl-5-formylcytidin (f5Cm), unknown modified guanosine (?G), 2'-O-(5phospho) ribosylguanosine (Gr(p)), 1-methylguanosine (m1G), $N^2$-methylguanosine (m2G), 2'-O-methylguanosine (Gm), $N^2N^2$-dimethylguanosine (m22G), $N^2,N^2,$2'-O-trimethylguanosine (m22Gm), 7-methylguanosine (m7G), archaeosine (fa7d7G), queuosine (Q), mannosyl-queuosine (manQ), galactosyl-queuosine (galQ), wybutosine (yW), peroxywybutosine (02yW), unknown modified uridine (?U), 5-methylaminomethyluridine (mnm5U), 2-thiouridine (s2U), 2'-O-methyluridine (Urn), 4-thiouridine (s4U), 5carbamoylmethyluridine (ncm5U), 5-methoxycarbonylmethyluridine (mcm5U), 5methylaminomethyl-2-thiouridine (mnm5s2U), 5-methoxycarbonylmethyl-2-thiouridine (mcm5s2U), uridine 5-oxyacetic acid (cmo5U), 5-methoxyuridine (mo5U), 5carboxymethylaminomethyluridine (cmnm5U), 5-carboxymethylaminomethyl-2-thiouridine (cmnm5s2U), 3-(3-amino-3-carboxypropyl) uridine (acp3U), 5-(carboxyhydroxymethyl)uridinemethyl ester (mchm5U), 5-carboxymethylaminomethyl-2'-O-methyluridine (cmnm5Um), 5-carbamoylmethyl-2'-O-methyluridine (ncm5Um), Dihydrouridine (D), pseudouridine (ψ), 1-methylpseudouridine (m1ψ), 2'-O-methylpseudouridine (ψm), ribosylthymine (m5U), 5-methyl-2-thiouridine (m5s2U), and 5,2'-O-dimethyluridine (m5Um).

In one embodiment, the modified nucleosides are mnm5s2U, mcm5s2U, ms2t6A, s2U, ψ, or t6A.

One specific tRNA fragment comprises the nucleic acid sequence 5'-CU(mnm5 s2U)UU(ms2t6A)A('1')CUGC.

Another specific tRNA fragment comprises the nucleic acid sequence 5'-GCU(mnm5 s2U)UU(ms2t6A)A('1')CUG.

Any of these tRNA fragments can further comprise a label. The label can be detectable, either directly or indirectly, by spectroscopic, photochemical, biochemical, immunochemical, or chemical means.

Representative labels include radioactive isotopes (for example, $^{32}$P, $^{35}$S, and $^3$H), dyes, fluorescent dyes (for example, Cy5 and Cy3), fluorophores (for example, fluorescein), electron-dense reagents, enzymes and their substrates (for example, as commonly used in enzyme-linked immunoassays, such as, alkaline phosphatase and horse radish peroxidase), biotin-streptavidin, digoxigenin, or hapten; and proteins for which antisera or monoclonal antibodies are available. The label can also be an "affinity tag."

Where the label comprises an affinity tag, the isolated tRNA fragments can be captured with a complimentary ligand coupled to a solid support that allows for the capture of the affinity tag-labeled tRNA fragment. Representative affinity tags and complimentary partners include biotin-streptavidin, complimentary nucleic acid fragments (for example, oligo dT-oligo dA, oligo T-oligo A, oligo dO-oligo dC, oligo O-oligo C), aptamers, or haptens and proteins for which antisera or monoclonal antibodies are available.

When a biological interaction brings the beads together, a cascade of chemical reactions acts to produce a greatly amplified signal. On laser excitation, a photosensitizer in the "Donor" bead converts ambient oxygen to a more excited singlet state. The singlet state oxygen molecules diffuse across to react with a thioxene derivative in the Acceptor bead generating chemiluminescence at 370 nm that further activates fluorophores contained in the same bead. The fluorophores subsequently emit light at 520-620 nm.

In one example of a commercially-available alpha bead, the Donor beads comprise biotin or are directly bound to RNA. The Acceptor beads include a His6 tag, hemagglutinin (HA), digoxin/digoxigenin (DIG), or fluorescein (FITC).

VII. Synthetic Methods for Producing Isolated Ribonucleotides

A variety of methods are known in the art for making nucleic acids having a particular sequence or that contain particular nucleic acid bases, sugars, internucleoside linkages, chemical moieties, and other compositions and characteristics. Anyone or any combination of these methods can be used to make a nucleic acid, polynucleotide, or oligonucleotide for the present invention. Said methods include, but are not limited to: (1) chemical synthesis (usually, but not always, using a nucleic acid synthesizer instrument); (2) post-synthesis chemical modification or derivatization; (3) cloning of a naturally occurring or synthetic nucleic acid in a nucleic acid cloning vector (e.g., see Sambrook, et al., Molecular Cloning: A Laboratory Approach 2nd ed., Cold Spring Harbor Laboratory Press, 1989) such as, but not limited to a plasmid, bacteriophage (e.g., mB or lamda), phagemid, cosmid, fosmid, YAC, or BAC cloning vector, including vectors for producing single-stranded DNA; (4) primer extension using an enzyme with DNA template-dependent DNA polymerase activity, such as, but not limited to, Klenow, T4, T7, rBst, Taq, Tfl, or Tth DNA polymerases, including mutated, truncated (e.g., exo-minus), or chemically-modified forms of such enzymes; (5) PCR (e.g., see Dieffenbach, C. W., and Dveksler, eds., PCR Primer: A Laboratory Manual, 1995, Cold Spring Harbor Laboratory Press, Cold Spring Harbor, N.Y.); (6) reverse transcription (including both isothermal synthesis and RT-PCR) using an enzyme with reverse transcriptase activity, such as, but not limited to, reverse transcriptases derived from avian myeloblasosis virus (AMV), Maloney murine leukemia virus (MMLV), *Bacillus stearothermophilus* (rBst), *Thermus thermophilus* (Tth); (7) in vitro transcription using an enzyme with RNA polymerase activity, such as, but not limited to, SP6, T3, or T7 RNA polymerase, Tth RNA polymerase, *E. coli* RNA polymerase, or another enzyme; (8) use of restriction enzymes and/or modifying enzymes, including, but not limited to exo- or endonucleases, kinases, ligases, phosphatases, methylases, glycosylases, terminal transferases, including kits containing such modifying enzymes and other reagents for making particular modifications in nucleic acids; (9) use of polynucleotide phosphorylases to make new randomized nucleic acids; (10) other compositions, such as, but not limited to, a ribozyme ligase to join RNA molecules; and/or (11) any combination of any of the above or other techniques known in the art. Oligonucleotides and polynucleotides, including chimeric (i.e., composite) molecules and oligonucleotides with non-naturally-occurring bases, sugars, and internucleoside linkages are commercially available (e.g., see the 2000 Product and Service Catalog, TriLink Biotechnologies, San Diego, Calif., USA)

The tRNA fragment or the target nucleic acid, or both the tRNA fragment and the target nucleic acid molecule may be detectably labeled to facilitate detection. In a preferred aspect, the tRNA fragment is labeled with a fluorophore to facilitate detection. In another aspect, the target nucleic acid molecule is labeled with biotin to facilitate detection. In another preferred aspect, the tRNA fragment is labeled with a fluorophore and the target nucleic acid molecule is labeled with biotin.

The tRNA fragment and target nucleic acid molecule may be labeled, for example, at either the 5' terminus, the 3'-terminus, or combinations of the 5'-terminus and the 3' terminus to facilitate detection. In addition, the test compound may also be labeled. In another embodiment, the tRNA fragment and the target nucleic acid molecule may have a detectable label attached to an internal position of the molecule to facilitate detection.

VIII. Methods for Detecting Binding (or Inhibition Thereof) of Target RNA to tRNA The methods for detecting binding of the target RNA to the tRNA or the inhibition of such binding may be performed using any method for such detection. For example, the AlphaScreen® assay (Packard Instrument Company, Meriden, Conn.). AlphaScreen® technology is an "Amplified Luminescent Proximity Homogeneous Assay" method utilizing latex microbeads (250 nm diameter) containing a photosensitizer (donor beads), or chemiluminescent groups and fluorescent acceptor molecules (acceptor beads). Upon illumination with laser light at 680 nm, the photosensitizer in the donor bead converts ambient oxygen to singlet-state oxygen. The excited singlet-state oxygen molecules diffuse approximately 250 nm (one bead diameter) before rapidly decaying. If the acceptor bead is in close proximity to the donor bead (i.e., by virtue of the interaction of the target RNA and tRNA fragment), the singlet-state oxygen molecules reacts with chemiluminescent groups in the acceptor beads, which immediately transfer energy to fluorescent acceptors in the same bead. These fluorescent acceptors shift the emission wavelength to 520-620 nm, resulting in a detectable signal. Antagonists of the interaction of the target RNA with the tRNA fragment will thus inhibit the shift in emission wavelength, whereas agonists of this interaction would enhance it.

The disclosed methods may be performed by mixing the component nucleotide (e.g. the tool tRNA and the target RNA) and the test compound in any order, or simultaneously. For example, a target RNA may be first combined with a test compound to form a first mixture, and then a tool tRNA fragment may be added to form a second mixture. In another example, a target RNA, a tool tRNA and the test compound may all be mixed at the same time before incubation. In one aspect, the mixture is incubated under conditions that allow binding of the tRNA fragment and the target nucleic acid in the absence of the test compound.

The inhibition of binding of the tRNA fragment and the target nucleic acid molecule by the test compound may be detected using any method available for the detection of inhibition. In one aspect, the determining step may be performed using methods including, but not limited to, gel shift assays, chemical and enzymatic footprinting, circular dichroism and NMR spectroscopy, equilibrium dialysis, or in any of the binding detection mechanisms commonly employed with combinatorial libraries of probes or test compounds. The inhibition of binding indicates that the test compound may be useful for inhibiting propagation of the virus in the host.

The invention will be further explained by the following illustrative examples, which are intended to be non-limiting.

EXAMPLES

Example 1

Synthesis of Linear tRNA Anticodon Stem Loop Sequences

The first step in producing the fragment tRNA anticodon stem loop (ASL) sequences is the synthesis of the modified nucleotides, also known as phosphoramidites (Agris et. al *Biochimie*. (1995) 77(1-2):125-34). The modified nucleotides are then used during the synthesis of the RNA oligomers (Ogilvie et. al. *Proc Natl Acad Sci USA*. (1988) 85:5764-8). Synthetic approaches overcome the substantial barrier of obtaining sufficient amounts of natural products for the functional characterization studies. In addition to providing the fully modified ASL for characterization of the fragment tRNA:target nucleotide binding, the synthetic approach allows for the preparation of intermediate steps/forms of the modified material that can further elucidate the individual contribution of each modification step in enhanced tRNA binding.

Modified base nucleic acid molecules were prepared using a combination of methods for the synthesis, incorporation, and purification of all the modified nucleotides found in the $ASL^{Lys3}$ human tRNA. Modified base phosphoramidites were prepared using known methods, such as those disclosed in Ogilive et. al., 1988. The $ASL^{Lys3}$ contains 3 modified bases denoted as mcm5s2U, ms2t6A and pseudouridine. Synthesis of the phosphoramides needed for the preparation of the synthetic mimics is described below in detail. Protocols for the polymers synthesis follow those developed for automated RNA synthesis (Ogilive et. al., 1988) with variations specific to the synthesis of the $ASL^{Lys3}$ mimics described below. The description includes methods for the removal of protection group required for automated synthesis and purification of the final products used in the assay.

The protecting group is subsequently removed after synthesis of the RNA oligomer. The addition of a protecting group to each modified base and ribose is described. While 2 position thio-groups can be oxidized in standard RNA synthesis protocols this has been overcome by using the tert-butyl hydroperoxide (10% solution in acetonitrile) oxidizing agent (Kumar and Davis, 1997). These synthetic RNA oligomers have been used in both functional (Yarian 2002 and Phelps 2004) and structural studies (Stuart 2000 and Murphy 2004).

Example IA

The Synthesis of the Protected Monomer Phosphoramidites mcm5s2U

The mcm5s2U nucleoside was prepared following published methods (Reese and Sanghvi 1984). Briefly, 2 thiouridine was heated with 5 molar equivalents each of pyrrolidine and formaldehyde in aqueous solution for 1 h, under reflux, resulting in 2',3'-0isopropylidene-5-pyrrolidinomethyl-2-thiouridine. This base was subsequently treated with 10 molar equivalents of methyl iodide in acetonitrile at room temperature. After 16 hours, the products were concentrated under reduced pressure to give the putative methiodide which was then dissolved in acetonitrile and allowed to react with 3 molar equivalents of glycine t-butyl ester' at room temperature for 16 h. This product was then purified and protection of the ribose and phosphitylation follow the general scheme described below.

ms2t6A

The monomer was obtained by condensation of the 2',3', 5'-O-triacetyl derivative of ms2A with the isocyanate derived from L-threonine-O-t-butyldimethylsilyl (TBDMS)-pnitrophenylethyl ester, under conditions which eliminate racemization of the amino acid. The product was selectively deprotected at the sugar moiety. Standard procedures were employed for final protection of the 5'-O- and 2'-O-functions with dimethoxytrityl (DMTr) and with TBDMS groups, respectively, as well as for 3'-O-phosphitylation (Agris et al., 1995).

S2U

The thio group was not protected in this synthesis. Protection of the ribose and phosphitylation follow the general scheme in panel C of FIG. 1. Protection of the ribose and phosphitylation follow the general scheme described below.

The sugar-protected phenyl carbamate 6 of t6A nucleoside was synthesized from 1-O-acetyl-2,3,5-tri-O-benzoylribofuranose The carbamate was treated with L-threonine to furnish the sugar-protected t6A nucleoside using the method of Hong and Chheda The remaining synthetic transformations followed general scheme described below.

Example IB

General Procedure for Ribose Protection and Phosphitylation

Methods for the protection of the modified nucleotide bases prior to synthesis of the RNA oligomer are provided (FIG. 1). Panel A of FIG. 1 illustrates protection with trifluoryl acetic acid. Panel B illustrates protection with benzoyl, and panel C illustrates the general protection of the ribose hydroxyl groups.

After base protection the scheme for the synthesis of 5'-O-(4,4'-dimethoxytrityl)-2'-O-tertbutyidimethylsilyi-modified ribonucleoside-3'-O-(2-cyanoethyl-N-diisopropyl)phosphoramidites is the same for both modified nucleotides (Panel C, FIG. 1). The protected nucleoside was dried by co-evaporation twice with pyridine and dissolved in pyridine. Tert-butyldimethylchlorosilane and imidazole were added and reacted for 4 hours at room temperature. The excess silyl chloride was decomposed with water and dichloromethane. The aqueous layer was extracted twice with dichloromethane and combined with the organic layer. The solvent was evaporated by vacuum yielding a gum which is then dissolved in ether and precipitated by pouring slowly into petroleum ether (4060° C.) with stirring. The precipitate was collected and washed twice with petroleum ether. At this point the crude product contains three components; the 2',3' disilylated, 2' silylated (major product) and 3' silylated isomers. The pure 2' protected isomer was purified by silica gel column chromatography. This product is then ready for phosphitylation.

The N-protected-5'-O-dimethoxytrityl-2'-O-tert-butyldimethylsilylribonucleosides were dried by two co-evaporations with anhydrous pyridine and THF. The residue was then dissolved in anhydrous THF under argon. Dimethylaminopyridine, N,N,N-ethyldiisopropylamine and cyanoethoxydiisopropy amino-chlorophosphine were added through a rubber septum. After 2 hours the reaction mixture, was quenched with ethyl acetate and washed with 5% sodium bicarbonate followed by water. Aqueous washes were back extracted with ethyl acetate. Combined organic layers were dried over sodium sulphate. Solvent was evaporated yielding a viscous oil. The product was co-evaporated twice with toluene and the pale yellow phosphoramidite products were purified by flash silica gel chromatography.

Example IC

Protocols for the Synthesis of the Modified RNA Polymers

The synthesis of the RNA followed standard protocols for a 1 mol scale by solid phase b-cyanoethyl phosphoramidite chemistry with 2'-OTBDMS protection (Usman et al., 1987), and N-4-tbutyl phenoxyacetyl (tac) protection of A, G and C monomers (Sinha et al., 1993). A, G, C and U monomers with tac and 2'-O-TBDMS protection and rC(tac)-succinyl controlled pore glass (CPG) support with the following variations. Addition of the unmodified A, C, G and U monomers were coupled in 5-fold molar excess for 6 min in the presence of 0.3 M 5-(benzylthio)-IH-tetrazole in acetonitrile (Welz and Muller, 2002), whereas mcm5s2U and ms2t6A monomers were used in 3-fold excess and coupled for 10 min. Following the coupling, a 2 min capping was performed with tac anhydride and then a 3 min oxidation with 1M cumene hydroperoxide in toluene. At the end of the synthesis the 5'dimethoxytrityl group was left in place.

Example ID

Protocols for the Deprotection of the Intermediates

The deprotection of the RNA was carried out in 3 steps as follows. The argon dried CPG carrying the fully protected RNA was treated with 20 ml of absolutely anhydrous 10% 1,8-diazabicyclo[5.4.0]undec-7-ene (DBU) in tetrahydrofuran for 45 min at 45° C. to beliminate the p-nitrophenylethyl and 2-cyanoethyl protecting groups. The supernatant was removed under a blanket of argon and the CPG was washed twice with dry THF. The CPG carrying partially deprotected RNA was then treated with 20 ml of 10% DBU in dry methanol under argon for 18 h at room temperature to cleave the nucleobase protecting groups and cleave the RNA from the CPG. The supernatant and methanol washings were dried in a Speedvac in a Falcon tube and then dried for 3 days in high vacuum (10)3 Torr) over phosphorus pentaoxide to remove the residual DBU. The 2'-O-TBDMS protected RNA was desilylated using 12 ml of triethylamine trihydrofluoride (Gasparutto et al., 1992) with vigorous stirring during 24 h at room temperature. During this step the DMT group is also removed from the 5'-terminal G residue. The reaction was quenched by addition of sterile water (1.2 ml) and the crude RNA was precipitated with butanol and kept at 20° C. for 24 h to complete the precipitation. The RNA was collected by centifugation, washed with butanol.

Example IE

Purification of the RNA Polymers

The synthetic RNA polymer products are purified by HPLC. The deprotected material is desalted using C18 SEP-PAK and purified by preparative anion-exchange HPLC using a gradient of sodium chloride. In some cases additional purification is required using reverse phase chromatography. To assure that the polymer product is correct it is analyzed by electrospray mass spectroscopy and nucleoside composition analysis.

Example II

Inhibitor Screening Assay

Figure 3:
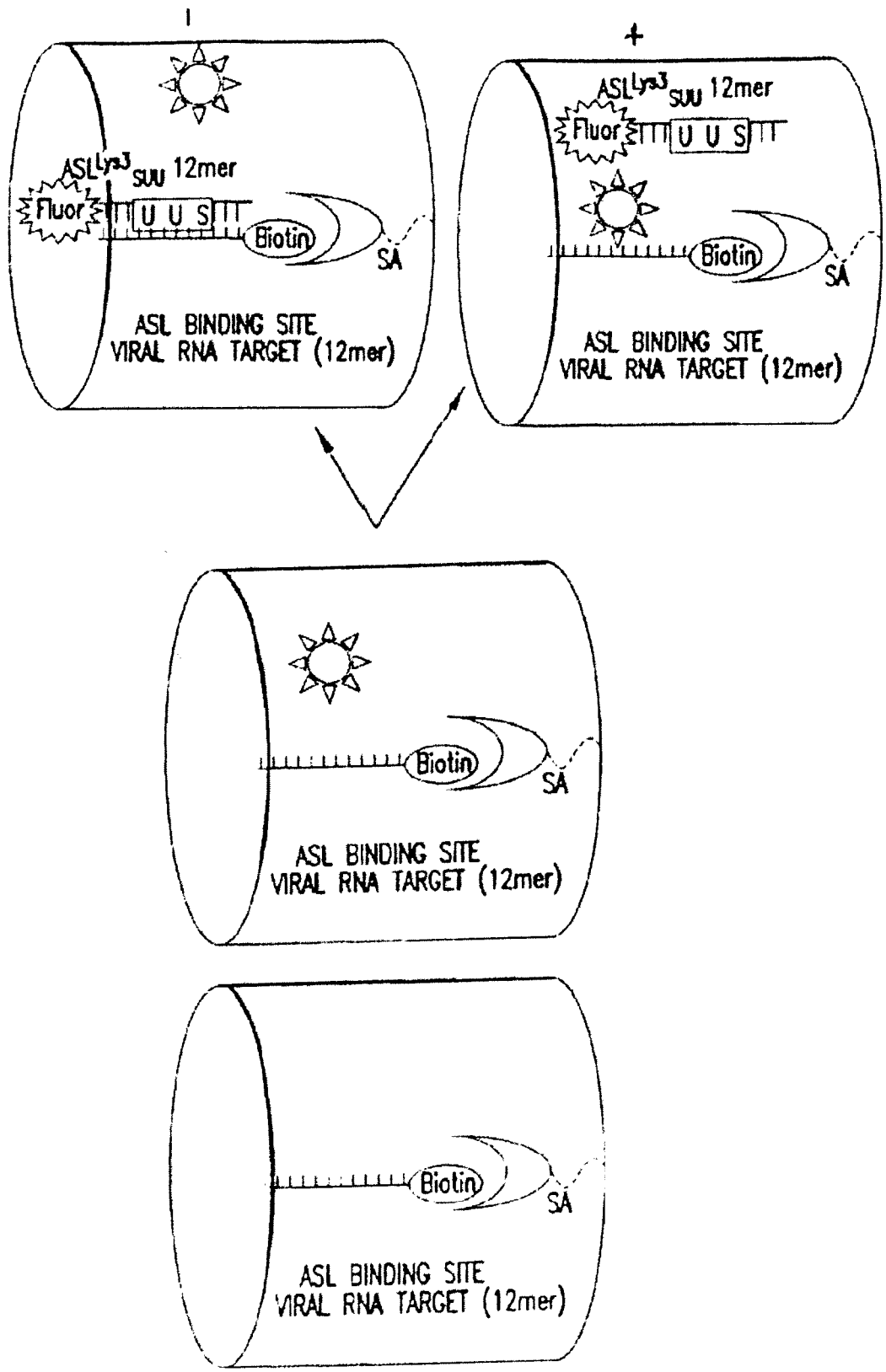
FIG. 3 provides a comparison of one example of an immobilized assay and an assay using the AlphaScreen™ assay.
Figure 3:
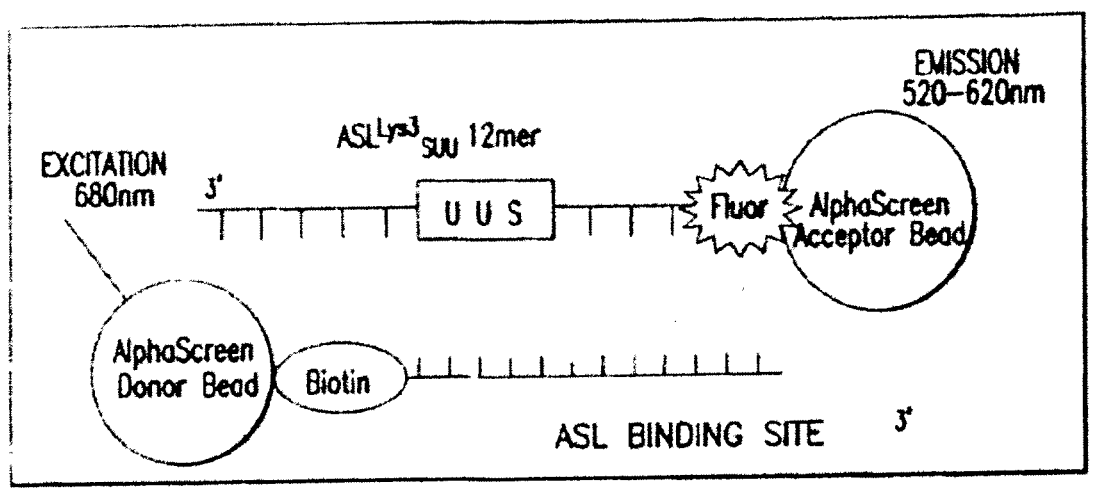

Two assays were developed using tool and target RNAs, the immobilized assay and the Alphascreen assay (FIG. 3). Both assays use the same two RNA components (the target RNA and the tRNA fragment). In the example, the HIV viral RNA target is a 12mer with a 3' Biotin, while the Human tRNA mimic is a synthetic 12mer containing the native modified nucleotides and 3' fluorescein. These two RNAs mimic an essential complex of the HIV replication complex.

As set forth more fully below, the immobilization assay uses a three step process that first involves the binding of the target RNA to an avidin coated microtiter plate. Then, the test compound (drug/small molecule), denoted as a star, is incubated with the target sequence for 30 min. Then, the tRNA mimic was added to determine if the complex was formed or inhibited. In this assay a phosphate buffer may be used with 1M NaCl to improve the affinity for the two RNA. The stability of the complex is concentration dependent so that μM concentrations are used and the assay is run at 4 degrees C.

The 5' labeled target RNA sequence (5'-CGGU-GUAAAAGC) is bound to a avidin microtiter plate (Roche High Load plates, 96-well avidin microtiter plates) by adding 150 μl of target solution to each well (FIG. 3, step A). The plates are covered and incubated at 37° C. for 1 hour. The plates are then rinsed twice with binding buffer, the second rinse is incubated at 37° C. for 5 minutes. The plates are then rinsed two additional times with binding buffer, covered, and ready for use.

The test compounds were prepared by thawing solutions of the compounds to room temperature. Dilutions of the test compounds (1:10 and 1:500) were prepared by dilution in DMSO and shaking for 1 hour.

The assays were performed by adding 98.5 μl of loading buffer (100 mM Tris HCl, pH 7.5, 150 mM NaCl and 0.1% Tween 20, pH adjusted from around 4.5 to 7.5 with 10 M NaOH) to each well of the plate. Test compounds were added individually to each well (1.5 μl each), and the plates were mixed for 1 hour (FIG. 3, step B).

Fifty microliters of solution containing the tool tRNA (5'-GCUXUUAYZCUG; where the X, Y, and Z are independently selected from modified nucleosides mnm5s2U, mcm5s2U, ms2t6A, s2U, ψ, and t6A) was then added to each well and the plates were incubated at 4° C. for 1 hour with shaking (FIG. 3, step C). The reaction mixture was then removed, while the mixture was still cold, and the remaining compound solution was also removed.

After removing the remaining solution, reading buffer (50 mM Hepes, pH 7.5, 100 mM NaCl, PEG (40 mg/200 ml)) was then added to each well and the results were read using a plate reader.

As shown in FIG. 3, a positive (+) reaction indicates that the test compound inhibits binding of the tool tRNA to the target nucleic acid (e.g. the test compound binds to either the tool tRNA, the target nucleic acid molecule or both the tool tRNA and the target nucleic acid molecule). A negative (−) reaction indicates that the test compound does not inhibit the binding of the tool tRNA to the target nucleic acid (e.g. the test compound does not bind to either the tool tRNA or the target nucleic acid).

In the AlphaScreen configuration (FIG. 3) the assay is done in solution using the same RNA as the immobilization assay. The donor and acceptor beads are bound to their respective RNA's. During the screening the RNAs and test drugs/small molecules are incubated together and formation of the complex is measured using the AlphaScreen detection conditions. Utilization of the AlphaScreen assay may allow for the assay to be run at a lower RNA concentration at room temperature, and increase the stability of the complex.

Example III

Validation of HIV Screening Assay

The HIV screening assay was validated to confirm that positive and negative controls would function as expected and to test a small compound library to verify that differential inhibition could be detected. Two validation runs were completed with 4,275 and 4,616 compounds, respectively, using 17 plates in each run. There were 3,961 compounds in common between the two assays and the statistical analysis was completed using only these compounds and the positive and negative controls. Each plate contained approximately 30 positive and 30 negative controls and these controls performed as expected. Differences were observed between validation runs when analyzing the luminescence; however, these differences were minimized or eliminated when evaluating the percent inhibition by compounds (hits) that were active in both runs. This assay met the functional requirements based on the results of the positive and negative controls.

To evaluate the inhibition exhibited in the screening of this small compound library, a cutoff was set at 42.96% inhibition, the average plus three times standard deviation of compound percent (%) inhibition. Using this cutoff, 34 repeated compounds (hits) were identified. By using 99.75% inhibition as the cutoff, the average minus three times standard deviation of positive control (Tool+Target) percent (%) inhibition, there is 1 repeated hit. If 29.02%, which is the average plus three times standard deviation of negative control (Tool) percent (%) Inhibition, is defined as the cutoff, there are 51 repeated hits, out of 3961 compounds analyzed. These results are in line with expectations when evaluating a small random compound library.

To select compounds for use in a secondary HIV assay to verify that this assay was capable of identifying HIV specific compounds with biological activity a cutoff was set at greater than 60% inhibition in at least one of the two validations runs. This resulted in the selection of 29 compounds. These compounds were analyzed for anti-HIV activity in freshly harvested PBMC cells. Of the 30 tested compounds, 15 were active at a concentration of less than 100~M (the highest tested concentration). Of these 15 compounds, 9 were not toxic to the PBMC cells at the 100~M concentration; thus, an absolute conclusion regarding the differential toxicity to HIV and PBMC cells cannot be drawn with these 9 compounds. Two other compounds had an antiviral index (inhibited HIV cells and not PBMC cells) greater than 25 which is acceptable.

Example IV

High Throughput Assay on a Large Compound Library

Biochemical HIV-1 tRNA Inhibition Assay:
HIV-1 has evolved to use Human tRNA$^{Lys3}$ as a primer for initiation of reverse transcription. Therefore, the interaction between tRNA$^{Lys3}$ and viral genomic RNA represents a potential novel target for HIV-1 drug development. Based on this hypothesis, a biochemical assay to identify inhibitors of the interaction between Human tRNA$^{Lys3}$ and HIV-1 genomic RNA was developed by TRANA Discovery and transferred to Southern Research Institute for high-throughput screening. This assay was developed as a homogeneous amplified luminescent proximity assay using AlphaScreen™ reagents from PerkinElmer. Based on this assay technology, the AlphaScreen™ luminescent signal serves as a mechanism for detecting the interaction between RNA molecules that represent Human tRNA$^{Lys3}$ and HIV-1 genomic RNA. The inhibition of the interaction between these RNA molecules by test compounds is detected as a decrease in the AlphaScreen™ luminescent signal.

Compounds Screened:
A preliminary 15,000 compound screen (NINDS Diversity Set) was previously completed and the results were reported through NIAID contract N01-AI-70042. For the results described herein, a 101,000 compound library that was purchased from ChemBridge for the NIAID TAACF program was used. This library was carefully selected for diversity and minimal similarity to the 100,000 compound NINDS library, which is also planned to be screened using the TRANA Discovery Biochemical HIV-1 tRNA Inhibition Assay. The compounds were screened at a concentration of 12.5 µg/mL (first 3 batches) or 25 µg/mL (fourth and final batch).

Results and Conclusions
Screening Results:
The median Z-value for the 78 assay plates used in the screen was 0.76, with a range from 0.64 to 0.86. Following analysis of the data, 99,303 valid screening results were obtained from all four compound batches screened. Statistical analysis identified 38.59% inhibition (batches 1-3 screened at 12.5 µg/mL) and 44.89% inhibition (batch 4 screened at 25 µg/mL) as the cutoffs between inactive and hit compounds. Based on these statistical criteria, a total of 315 compounds were identified as hits. There were 202 hits identified from the 75,144 compounds screened in compound batches 1-3 (hit rate of 0.27%). Similarly, there were 113 hits identified from the 24,159 compounds screened in compound batch 4 (hit rate of 0.47%). The resulting overall combined hit rate for the screen was 0.32%. The range of the percent inhibition observed for the 315 hits was from 38.59% to 99.66%. Overall, the statistical cutoffs and hit rate observed for this screen are somewhat lower than the values previously observed when screening the NINDS Diversity Set (72.31% and 1.09% for hit cutoff and hit rate, respectively). However, these general differences can be explained by the lower test concentrations and plate format used for this screen (12.5 and 25 µg/mL; 1536-well plates) compared to the NINDS Diversity Set (40 µg/mL; 384-well plates).

Dose-response Testing Results:
For initial follow-up testing of the compounds, resupplies of the hits were purchased from ChemBridge for dose-response testing in the TRANA Discovery biochemical HIV-1 tRNA inhibition assay. Of the 315 hits identified in the screen, 309 were available for resupply and were evaluated in dose-response, in duplicate. 183 hits (59.2%) were confirmed to be active in the assay. In addition, 125 hits (40.5%) reached an $IC_{50}$ value within the concentration range evaluated (0.049-25 µg/mL). The observed $IC_{50}$ values ranged from 0.205 to 24.97 µg/mL.

An additional 200,000 compounds were tested, of which 30,000 compounds came from an Enamine RDS library, and of which 170,000 compounds came from three compound sets (totaling 174,441 compounds), including 1) a 99,680 compound library purchased from Enamine 2) a 25,588 compound "Kinase" library purchased from Life Chemicals (LC Kinase), and 3) a 49,173 compound ChemBridge CNS subset of the NINDS library. Based on the results of the high throughput screening using these libraries, 1,117 compounds were identified as hits. These hits were cherry-picked from the compound library plates for follow-up testing in dose-response in the TRANA Discovery Biochemical HIV-1 tRNA Inhibition Assay as well as in a cytotoxicity assay using the human monocyte cell line, THP-1. Based on the dose-response testing of hits, 93 compounds that achieved an IC50 value of less than 25 µg/mL in the TRANA Discovery HIV-1 tRNA biochemical inhibition assay and that were not toxic in the THP-1 cytotoxicity assay were identified for additional follow-up testing. Eighty-eight (88) of these compounds were available for re-supply from the library suppliers and purchased in larger quantities for testing against HIV-1IIIB replication in a CEM-SS cytoprotection assay using a 100 µM high-test concentration. AZT was included in the CEM-SS cytoprotection assay as a positive control antiviral compound.

The active compounds are listed below, with those compounds showing some activity marked with a "+," those with intermediate activity marked with a "++," and those with the highest activity marked with a "+++."

ethyl 5-amino-2-(6-hydroxy-3-oxo-3H-xanthen-9-yl)benzoate
Activity: +++
1-(1-pyrrolidinyl)anthra-9,10-quinone
1-Pyrrolidin-1-yl-anthraquinone
++
ethyl (3-oxo-4,5-diphenyl-1,3-dihydro-2H-pyrrol-2-ylidene)acetate
Activity: ++
1-methyl-4-(1-piperidinyl)anthra-9,10-quinone
1-Methyl-4-piperidin-1-yl-anthraquinone
Activity: ++
2-[(3-methylphenyl)amino]-3-(4-morpholinyl)naphthoquinone
Activity: ++
2-[(3-fluorophenyl)amino]-3-(1-pyrrolidinyl)naphthoquinone
Activity: ++
N-(4-ethoxy-8-methyl-2-quinazolinyl)guanidine
Activity: ++
2-[(2-methylphenyl)amino]-3-(4-morpholinyl)naphthoquinone
Activity: ++
2-[(3-methylphenyl)amino]-3-(1-pyrrolidinyl)naphthoquinone
Activity: ++
2-[(3-methoxyphenyl)amino]-3-(1-piperidinyl)naphthoquinone
Activity: ++
2-[(3-methoxyphenyl)amino]-3-(4-morpholinyl)naphthoquinone
Activity: ++
1-(dimethylamino)anthra-9,10-quinone
1-Dimethyl amino-anthraquinone
Activity: ++
2-[(3-chlorophenyl)amino]-3-(4-morpholinyl)naphthoquinone
Activity: ++
ethyl 4-{[3-(4-morpholinyl)-1,4-dioxo-1,4-dihydro-2-naphthalenyl]amino}benzoate
Activity: ++
methyl 4-{[1,4-dioxo-3-(1-pyrrolidinyl)-1,4-dihydro-2-naphthalenyl]amino}benzoate
Activity: ++
1-(4-hydroxyphenyl)-1-propanone(2-nitrophenyl)hydrazone
Activity: ++
4-[(7-nitro-2,1,3-benzoxadiazol-4-yl)amino]phenol
Activity: ++
4,4,8-trimethyl-1-{[2-(4-nitrophenyl)-2-oxoethyl]thio}-4,5-dihydro[1,2]dithiolo[3,4-c]quinolin-2-ium chloride
Activity: ++
2-[(4-acetylphenyl)amino]-3-(1-pyrrolidinyl)naphthoquinone
Activity: ++
3,4-dihydroxybenzaldehyde(2-nitrophenyl)hydrazone
Activity: ++
2,6-dimethyl-4-[(4-methylphenyl)amino]phenol
Activity: ++
5-(3,4-dihydroxybenzylidene)-3-(3-fluorophenyl)-2-thioxo-1,3-thiazolidin-4-one
Activity: ++
methyl 9,10-dioxo-4-(1-piperidinyl)-9,10-dihydro-1-anthracenecarboxylate
Activity: ++
2-[(3-methoxyphenyl)amino]-3-(1-pyrrolidinyl)naphthoquinone
Activity: ++
2-[(7-nitro-2,1,3-benzoxadiazol-4-yl)amino]phenol
Activity: ++
2-chloro-3-(dimethylamino)naphthoquinone
Activity: ++
methyl 4-{[3-(4-morpholinyl)-1,4-dioxo-1,4-dihydro-2-naphthalenyl]amino}benzoate
Activity: ++
1-(3-methylphenyl)-5-[(1-methyl-1H-pyrrol-2-yl)methylene]-2-thioxodihydro-4,6(1H,5H)-pyrimidinedione
Activity: ++
8-ethoxy-4,4-dimethyl-1-(methylthio)-4,5-dihydro[1,2]dithiolo[3,4-c]quinolin-2-ium chloride
Activity: ++
2-[(3,5-difluoropheny)amino]-3-(4-morpholinyl)naphthoquinone
Activity: ++
2-(dimethylamino)-3-[(3-methylphenyl)amino]naphthoquinone
Activity: ++
5-(2,6-dichloro-3-nitrobenzylidene)-3-methyl-2-thioxo-1,3-thiazolidin-4-one
Activity: ++
5-(3,4-dihydroxybenzylidene)-3-ethyl-2-thioxo-1,3-thiazolidin-4-one
Activity: +
N-(4-ethoxyphenyl)-7-nitro-2,1,3-benzoxadiazol-4-amine
Activity: +
2-[(3,4-difluorophenyl)amino]-3-(4-morpholinyl)naphthoquinone
Activity: +
N,N-dimethyl-N'-(7-methyl-2,3-dihydro-1H-cyclopenta[b]quinolin-9-yl)-1,4-benzenediamine
Activity: +
1-(4-chlorophenyl)-5-(2-furylmethylene)-2-thioxodihydro-4,6(1H,5H)-pyrimidinedione
Activity: +
5-(2-furylmethylene)-1-(1-naphthyl)-2,4,6(1H,3H,5H)-pyrimidinetrione
Activity: +
N-[4-(dimethylamino)benzyl]-N,N',N-triethyl-1,2-ethanediamine
Activity: +
3-allyl-5-(3,5-dichloro-2-hydroxybenzylidene)-2-thioxo-1,3-thiazolidin-4-one
Activity: +
2-chloro-3-(isopropylamino)naphthoquinone
Activity: +
2-[(3-hydroxypheny)amino]-3-(1-piperidinyl)naphthoquinone
Activity: +
N,N-diethyl-N'-[4-(2-pyridinyl)-1,3-thiazol-2-yl]-1,4-benzenediamine hydrobromide
Activity: +
N-(7-methoxy-4-methyl-2-quinazolinyl)guanidine
Activity: +
3-nitrobenzaldehyde 1,2-ethanediyl(methylhydrazone)
Activity: +
3-amino-5-(3,4-dihydroxybenzylidene)-2-thioxo-1,3-thiazolidin-4-one Activity: +
2-(benzylamino)-3-chloronaphthoquinone
Activity: +
1-amino-2-chloro-4-(1-pyrrolidinyl)anthra-9,10-quinone
1-Amino-2-chloro-4-pyrrolidin-1-yl-anthraquinone
Activity: +
N-({[4-(diethylamino)phenyl]amino}carbonothioyl)-3-isopropoxybenzamide
Activity: +
5-acetyl-8-ethoxy-4,4-dimethyl-4,5-dihydro-1H-[1,2]dithiolo[3,4-c]quinoline-1-thione
1-(8-Ethoxy-4,4-dimethyl-1-thioxo-1,3a,4,9b-tetrahydro-2,3-dithia-5-aza-cyclopenta[a]naphthalen-5-yl)-ethanone
Activity: +
1-(3-chlorophenyl)-5-(2-furylmethylene)-2-thioxodihydro-4,6(1H,5H)-pyrimidinedione
Activity: +
1-(4-chlorophenyl)-5-[(1-methyl-1H-pyrrol-2-yl)methylene]-2-thioxodihydro-4,6(1H,5H)-pyrimidinedione
Activity: +
1,3-benzodioxol-5-yl(3-methylbenzyl)amine
Activity: +
(4-{3-[4-(2-methoxyphenyl)-1-piperazinyl]-1-propen-1-yl}phenyl)dimethylamine
Activity: +
ethyl 2-(7-bromo-3,4-dioxo-3,4-dihydro-1-naphthalenyl)-3-oxo-3-phenylpropanoate
Activity: +
5-acetyl-4,4,8-trimethyl-4,5-dihydro-1H-[1,2]dithiolo[3,4-c]quinoline-1-thione
1-(4,4,8-Trimethyl-1-thioxo-1,3a,4,9b-tetrahydro-2,3-dithia-5-aza-cyclopenta[a]naphthalen-5-yl)-ethanone
Activity: +
1-(2-furyl)ethanone (2-nitrophenyl)hydrazone
Activity: +
5-acetyl-8-methoxy-4,4-dimethyl-4,5-dihydro-1H-[1,2]dithiolo[3,4-c]quinoline-1-thione
1-(8-Methoxy-4,4-dimethyl-1-thioxo-1,3a,4,9b-tetrahydro-2,3-dithia-5-aza-cyclopenta[a]naphthalen-5-yl)-ethanone
Activity: +
2-[(4,7-dimethyl-2-quinazolinyl)amino]-6-methyl-4-pyrimidinol
Activity: +
2-amino-3-[(2-methylphenyl)amino]naphthoquinone
Activity: +
1-(5-chloro-2-nitrophenyl)-4-(4-methoxyphenyl)piperazine
Activity: +
1-(4-chlorophenyl)-5-[(5-nitro-2-furyl)methylene]-2-thioxodihydro-4,6(1H,5H)-pyrimidinedione
Activity: +
5-(3,4-dihydroxybenzylidene)-3-phenyl-2-thioxo-1,3-thiazolidin-4-one
Activity: +
3-butoxy-N-({[4-(dimethylamino)phenyl]amino}carbonothioyl)benzamide
Activity: +
2-bromo-N-[5-(3,4-dihydroxybenzylidene)-4-oxo-2-thioxo-1,3-thiazolidin-3-yl]benzamide
Activity: +
5-methyl-2-furaldehyde(2-nitrophenyl)hydrazone
Activity: +
N-(4,8-dimethyl-2-quinazolinyl)guanidine
Activity: +
2-[(2-hydroxyethyl)amino]-3-[(3-methylpheny)amino]naphthoquinone
Activity: +
1-[(2,2,6,6-tetramethyl-4-piperidinyl)amino]anthra-9,10-quinone
1-[1-(2,2-Dimethyl-propyl)-3,3-dimethyl-butylamino]-anthraquinone
Activity: +
6-(5-methyl-2-oxo-2,3-dihydro-1H-imidazol-4-yl)-6-oxo-hexanoic acid
Activity: +++
ethyl 6-(5-methyl-2-oxo-2,3-dihydro-1H-imidazol-4-yl)-6-oxohexanoate
Activity: ++

These compounds have been prioritized based on their $IC_{50}$ values and were subjected to dose-response testing against HIV-1$_{IIIB}$ replication in a CEM-SS cytoprotection assay, as shown below in Example V.

Example V

High Throughput In Vivo Assay—Efficacy Evaluation in CEM-SS Cells a. Anti-HIV-1 Cytoprotection Assay Cell Preparation—CEM-SS cells were passaged in T-75 flasks prior to use in the antiviral assay. On the day preceding the assay, the cells were split 1:2 to assure they were in an exponential growth phase at the time of infection. Total cell and viability quantification was performed using a hemacytometer and trypan blue exclusion. Cell viability was greater than 95% for the cells to be utilized in the assay. The cells were resuspended at $5\times10^4$ cells/mL in tissue culture medium and added to the drug-containing microtiter plates in a volume of 50 µL.

Virus Preparation—The virus used for this test was the lymphocytropic virus strains HIV-1IIIB. The virus was obtained from the NIH AIDS Research and Reference Reagent Program and was grown in CEM-SS cells for the production of stock virus pools. For each assay, a pre-titered aliquot of virus was removed from the freezer (−80° C.) and allowed to thaw slowly to room temperature in a biological safety cabinet. The virus was resuspended and diluted into tissue culture medium such that the amount of virus added to each well in a volume of 50 µL was the amount determined to give between 85 to 95% cell killing at 6 days post-infection. $TCID_{50}$ calculations by endpoint titration in CEM-SS cells indicated that the multiplicity of infection of these assays was approximately 0.01.

The table below shows the plate format used in the assay:

| | 1 | 2 | 3 | 4 | 5 | 6 | 7 | 8 | 9 | 10 | 11 | 12 |
|---|---|---|---|---|---|---|---|---|---|---|---|---|
| A | | Reagent Background Control Wells (Media plus MTS, no cells) | | | | | | Plastic Background Control Wells (Media only, no cells) | | | | |
| B | | Tox 1 0.32 µM | Cell Control | Drug 1 Low-Test 0.32 µM | | Tox 1 0.32 µM | Tox 2 0.32 µM | Drug 2 Low-Test 0.32 µM | | Cell Control | Tox 2 0.32 µM | |
| C | | Tox 1 1.0 µM | | Drug 1 1.0 µM | | Tox 1 1.0 µM | Tox 2 1.0 µM | Drug 2 1.0 µM | | | Tox 2 1.0 µM | |

|   | 1 | 2 | 3 | 4 | 5 | 6 | 7 | 8 | 9 | 10 | 11 | 12 |
|---|---|---|---|---|---|---|---|---|---|---|---|---|
| D | Tox 1 3.2 µM | | | Drug 1 3.2 µM | | Tox 1 3.2 µM | Tox 2 3.2 µM | | Drug 2 3.2 µM | | | Tox 2 3.2 µM |
| E | Tox 1 10 µM | Virus Control | | Drug 1 10 µM | | Tox 1 10 µM | Tox 2 10 µM | | Drug 2 10 µM | | Virus Control | Tox 2 10 µM |
| F | Tox 1 32 µM | | | Drug 1 32 µM | | Tox 1 32 µM | Tox 2 32 µM | | Drug 2 32 µM | | | Tox 2 32 µM |
| G | Tox 1 100 µM | | | Drug 1 High-Test 100 µM | | Tox 1 100 µM | Tox 2 100 µM | | Drug 2 High-Test 100 µM | | | Tox 2 100 µM |
| H | Color 1 100 µM | Color 1 32 µM | Color 1 10 µM | Color 1 3.2 µM | Color 1 1.0 µM | Color 1 0.32 µM | Color 2 100 µM | Color 2 32 µM | Color 2 10 µM | Color 2 3.2 µM | Color 2 1.0 µM | Color 2 0.32 µM |

Cells labeled as "Drug 1" or "Drug 2" = Cells + Virus + Drug (example dilution scheme indicated)
Cells labeled as "Tox 1" or "Tox 2" = Cells + Drug 1 or Drug 2, respectively (toxicity tested in duplicate)
Cells labeled as "Color 1" or "Color 2" = Media + Drug 1 or Drug 2, respectively (colorimetric background, no cells)

Plate Format—The format of the test plate is shown in the table above. Each plate contains cell control wells (cells only), virus control wells (cells plus virus), drug cytotoxicity wells (cells plus drug only), drug colorimetric control wells (drug only) as well as experimental wells (drug plus cells plus virus). As shown in the table above, 100 µM was used as a representative high-test concentration. Samples were evaluated for antiviral efficacy with triplicate measurements using 6 concentrations at half-log dilutions in order to determine $IC_{50}$ values and with duplicate measurements to determine cellular toxicity, if detectable.

b. MTS Staining for Cell Viability

At assay termination, the assay plates were stained with the soluble tetrazolium-based dye MTS (CellTiter 96 Reagent, Promega) to determine cell viability and quantify compound toxicity. MTS is metabolized by the mitochondrial enzymes of metabolically active cells to yield a soluble formazan product, allowing the rapid quantitative analysis of cell viability and compound cytotoxicity. This reagent is a stable, single solution that does not require preparation before use. At termination of the assay, 20-25 µl, of MTS reagent is added per well and the microtiter plates are then incubated for 4-6 hrs at 37° C., 5% $CO_2$ to assess cell viability. Adhesive plate sealers were used in place of the lids, the sealed plate was inverted several times to mix the soluble formazan product and the plate was read spectrophotometrically at 490/650 nm with a Molecular Devices Vmax plate reader.

c. Data Analysis

Using a proprietary computer program % CPE Reduction, % Cell Viability, compound concentrations resulting in the inhibition of virus replication by 25%, 50%, and 95% ($IC_{25}$, $IC_{50}$, and $IC_{95}$ values), compound concentrations resulting in 25%, 50%, and 95% cytotoxicity ($TC_{25}$, $TC_{50}$, and $IC_{95}$) and Antiviral Indices (=$TC_{25}/IC_{25}$, $TC_{50}/IC_{50}$, or $TC_{95}/IC_{95}$) were calculated and the graphical results summary was displayed. AZT was evaluated in parallel as a relevant positive control compound in the anti HIV assays.

RESULTS

The results from the testing of 88 lead compounds identified in in vitro assays against HIV-1IIIB replication in CEM-SS cells are summarized below. AZT was used as a positive control. Those compounds listed below had bioactivity in the assay.

Compound 82 has the structure shown below:

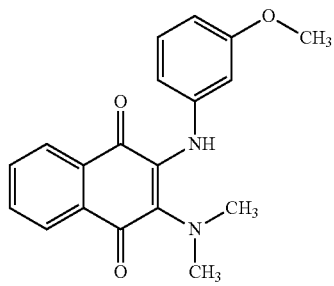 [SMILES: COc1cccc(NC2=C(N(C)C)C(=O)c3ccccc3C2=O)c1]

Compound 576 has the structure shown below:

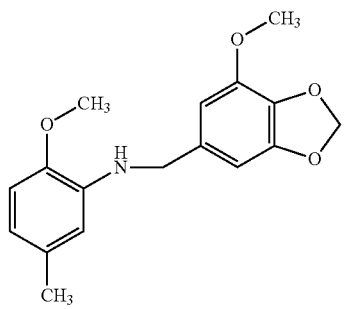 [SMILES: COc1ccc(C)cc1NCc1cc(OC)c2c(c1)OCO2]

Compound 374 has the structure shown below:

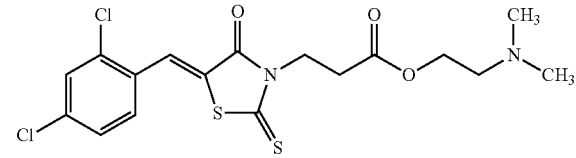 [SMILES: CN(C)CCOC(=O)CCN1C(=O)/C(=C/c2ccc(Cl)cc2Cl)SC1=S]

Compound 257 has the structure shown below:

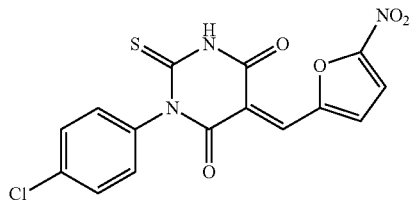 [SMILES: O=C1NC(=S)N(c2ccc(Cl)cc2)C(=O)/C1=C/c1ccc([N+](=O)[O-])o1]

Compound 259 has the structure shown below:

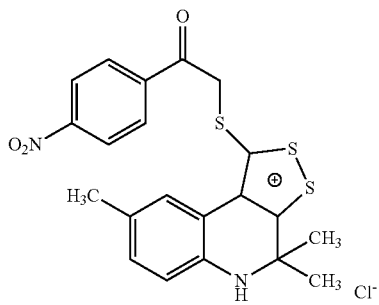 [SMILES: Cc1ccc2c(c1)C1C(SCC(=O)c3ccc([N+](=O)[O-])cc3)SSC1C(C)(C)N2 ; [Cl-]]

Compound 110 has the structure shown below:

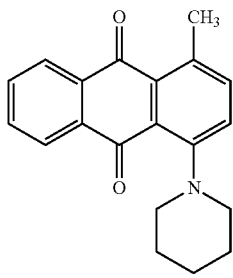 [SMILES: Cc1ccc(N2CCCCC2)c2c1C(=O)c1ccccc1C2=O]

Although the foregoing invention has been described in some detail by way of illustration and example for purposes of clarity of understanding, it will be obvious that certain changes and modifications may be practiced within the scope of the appended claims.

What is claimed is:

1. A pharmaceutical composition comprising a compound of one of the following formulas formula, in combination with a pharmaceutically acceptable carrier and in the form of a pill, tablet, capsule, or caplet:

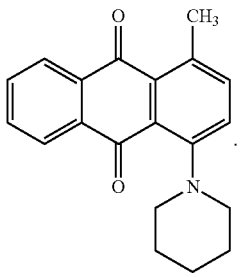 [SMILES: Cc1ccc(N2CCCCC2)c2c1C(=O)c1ccccc1C2=O]

2. The composition of claim 1, further comprising an additional antiviral agent.

3. The composition of claim 2, wherein the additional antiviral agent is an entry inhibitor, integrase inhibitor, reverse transcriptase inhibitor, protease inhibitor, or an immune-based therapeutic agent.

4. A method of treating a retroviral infection, comprising administering a compound of the following formula,

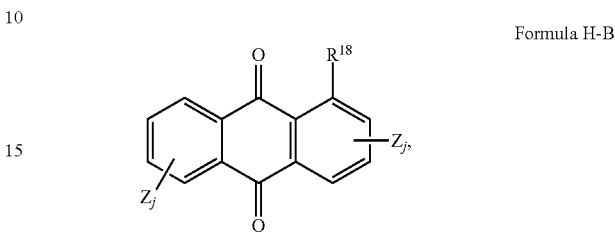

Formula H-B wherein:
Z is selected from the group consisting of $C_{1-6}$ alkyl, alkenyl, halo, —OR', —NR'R", —CF$_3$, —CN, —NO$_2$, $C_2R'$, —SR', —N$_3$, —C(=O)NR'R", —NR'C(=O)R", —C(=O)R', —C(=O)OR', —OC(=O)R', —OC(=O)NR'R", —NR'C(=O)OR", —SO$_2$R', —SO$_2$NR'R", and NR'SO$_2$R",
where R' and R" are individually hydrogen, $C_{1-6}$alkyl, cycloalkyl, aryl, or arylalkyl,
$R^{18}$ is a 4-8 membered ring azacycle, and
j is an integer from 0-3, to a patient in need of treatment thereof,
wherein the retroviral infection is HIV.

5. The method of claim 4, wherein the inhibitor inhibits retroviral reverse transcription.

6. The method of claim 4, wherein the inhibitor inhibits viral recruitment of the retroviral primer used in translation, human tRNA$^{Lys3}$.

7. The method of claim 4, wherein the inhibitor inhibits the final packaging and assembly of new virions.

8. The method of claim 4, wherein the inhibitor inhibits the binding of a host cell tRNA to a target nucleic acid molecule.

9. The method of claim 4, further comprising the co-administration of a second antiretroviral compound.

10. The method of claim 9, wherein the second antiretroviral agent is selected from the group consisting of NRTIs, NNRTIs, VAP anti-idiotypic antibodies, CD4 and CCR5 receptor inhibitors, entry inhibitors, antisense oligonucleotides, ribozymes, protease inhibitors, neuraminidase inhibitors, tyrosine kinase inhibitors, PI-3 kinase inhibitors, and Interferons.

11. The method of claim 4, wherein the HIV is selected from the group consisting of HIV-I, HIV-II, HIV-III (also known as HTLV-II, LAV-I, LAV-2), and mutated versions thereof.

* * * * *